United States Patent
Khatun et al.

(10) Patent No.: US 10,610,480 B2
(45) Date of Patent: Apr. 7, 2020

(54) PERSONAL CARE COMPOSITION FOR A KERATIN SUBSTRATE COMPRISING CONDITIONING, COLOR PROTECTING AND STYLING POLYMER

(71) Applicant: ISP Investments LLC, Wilmington, DE (US)

(72) Inventors: Amna Khatun, West Yorkshire (GB); Michael Franzke, Barendrecht (NL); Lidia Kulcsar, Flanders, NJ (US); Gijsbert Kroon, Hardinxveld-Giessendam (NL); Linda C. Foltis, Nutley, NJ (US)

(73) Assignee: ISP Investments LLC, Wilmington, DE (US)

( * ) Notice: Subject to any disclaimer, the term of this patent is extended or adjusted under 35 U.S.C. 154(b) by 0 days.

(21) Appl. No.: 16/084,607

(22) PCT Filed: Mar. 15, 2017

(86) PCT No.: PCT/US2017/022575
§ 371 (c)(1),
(2) Date: Sep. 13, 2018

(87) PCT Pub. No.: WO2017/161036
PCT Pub. Date: Sep. 21, 2017

(65) Prior Publication Data
US 2019/0099349 A1   Apr. 4, 2019

Related U.S. Application Data

(60) Provisional application No. 62/307,843, filed on Mar. 14, 2016.

(51) Int. Cl.
| | | |
|---|---|---|
| *A61K 8/81* | (2006.01) | |
| *A61Q 5/00* | (2006.01) | |
| *A61Q 5/06* | (2006.01) | |
| *A61Q 5/12* | (2006.01) | |
| *C08F 222/38* | (2006.01) | |
| *A61Q 5/02* | (2006.01) | |

(52) U.S. Cl.
CPC .......... *A61K 8/8147* (2013.01); *A61K 8/8158* (2013.01); *A61K 8/8188* (2013.01); *A61Q 5/004* (2013.01); *A61Q 5/02* (2013.01); *A61Q 5/06* (2013.01); *A61Q 5/12* (2013.01); *C08F 222/38* (2013.01); *A61K 2800/5424* (2013.01); *A61K 2800/5426* (2013.01)

(58) Field of Classification Search
CPC ... A61Q 5/02; A61Q 5/12; A61Q 5/06; A61Q 5/004; A61Q 19/00; A61Q 19/10; A61Q 1/02; A61K 8/817; A61K 2800/5426; A61K 8/8188; A61K 2800/95; A61K 8/8158; A61K 8/8182; A61K 8/8147; A61K 2800/5424; A61K 2800/10; A61K 2800/21; A61K 8/042; A61K 8/8152
See application file for complete search history.

(56) References Cited

U.S. PATENT DOCUMENTS

| | | | |
|---|---|---|---|
| 6,852,815 B1* | 2/2005 | Chuang | A61K 8/8182 526/264 |
| 2003/0022987 A1 | 1/2003 | Matz et al. | |
| 2013/0209388 A1 | 8/2013 | Erazo-Majewicz et al. | |
| 2013/0266531 A1* | 10/2013 | Yuan-Huffman | A61Q 19/00 424/70.16 |
| 2015/0297496 A1* | 10/2015 | Kroon | A61Q 5/06 424/54 |

FOREIGN PATENT DOCUMENTS

WO  WO 01/05851 A1   1/2001

OTHER PUBLICATIONS

International Search Report of PCT Application No. PCT/US2017/022575 published on Sep. 21, 2017.
Rigoletto et al. "Polyquaternium-69: A New Fixative Polymer with Enhanced Styling Benefits" 1-20 Cosmetic Science Technology—Polymers (2007): pp. 142-156.

* cited by examiner

*Primary Examiner* — Audrea B Coniglio
(74) *Attorney, Agent, or Firm* — William J. Davis; Nathalie Tietcheu

(57) ABSTRACT

A personal care conditioning, color protecting and/or styling composition for a keratin substrate comprising: (A) at least one conditioning and/or styling ter/tetra polymer obtained from polymerizing: (i) about 0.1 wt. % to 99 wt. % of acrylamidopropyl trimethylammonium chloride (APTAC), a cationic monomer; (ii) about 0.1 wt. % to 30 wt. % of at least one anionic monomer selected from the group consisting of (a) acrylic acid (AA), (b) acrylamido methylpropyl sulfonate (AMPS), and/or (c) sodium methyl allyl sulfonate (SMAS); and (iii) about 0.1 wt. % to about 20 wt. % of methacryloylaminopropyl lauryl-dimethyl ammonium chloride (MAPLDMAC), a hydrophobically modified cationic monomer; (B) at least one cosmetically acceptable excipient; and (C) optionally, at least one effective amount of personal care active ingredient.

20 Claims, 7 Drawing Sheets

| Hair Characteristic | Rating |
|---|---|
| Shine | 1 2 3 4 5 6 7 8 9 10<br>Very,            Average            Very,<br>Very dull            Shine            Very Shiny |
| Stiffness – 1st Compression<br>Compress Curl Between Fingers Once | 1 2 3 4 5 6 7 8 9 10<br>Very            Slightly            Very,<br>Very Soft            Soft            Very Stiff<br>(natural) |
| Crunch | 1 2 3 4 5 6 7 8 9 10<br>Very            Average            Very,<br>Very, Little            Crunch            Very<br>Crunch            Crunchy |
| Stiffness – 5th Compression<br>Compress Curl Between Fingers a Total of 5 Times | 1 2 3 4 5 6 7 8 9 10<br>Very,            Slightly            Very,<br>Very Soft            Soft            Very Stiff<br>(Natural) |
| Stiffness – 10th Compression<br>Compress Curl Between Fingers a Total of 10 Times | 1 2 3 4 5 6 7 8 9 10<br>Very,            Slightly            Very,<br>Very Soft            Soft            Very Stiff<br>(Natural) |
| Curl Snap – Hold Curl Between Fingers, Fully Extend Curl Then | 1 2 3 4 5 6 7 8 9 10<br>No            Fair            Excellent |

FIG. 5

| Release | Springback | Springback | Springback |
|---|---|---|---|
| Comb Drag Comb Tress 4 Times | 1　2　3　4<br>Very Difficult to Comb (Can't Get Comb Through) | 5　6　7<br>Moderately Difficult to Comb | 8　9　10<br>Very Easy to Comb |
| Residue on Comb (Powder or Flake After Combing) | 1　2　3　4<br>Very Large Amount of Residue | 5　6　7<br>Visible Flakes | 8　9　10<br>No Visible Residue |
| Residue on Hair (Flakes, White Powder) | 1　2　3　4<br>Very Heavy Residue | 5　6　7<br>Visible Flakes | 8　9　10<br>No Visible Residue |
| Manageability Comb Thru Tress with Fine Tooth of Comb. Remake Curl and Evaluate Curl | 1　2　3　4<br>Hair is Straight, Can't Remake Curl | 5　6　7<br>Slight Curl | 8　9　10<br>Very Tight Curl |
| Static - Comb Tress and Evaluate Static | 1　2　3　4<br>Total, Uncontrollable Flyaway | 5　6　7<br>Moderate Flyaway | 8　9　10<br>No Flyaway |

FIG. 5 (Cont.)

PERSONAL CARE COMPOSITION FOR A KERATIN SUBSTRATE COMPRISING CONDITIONING, COLOR PROTECTING AND STYLING POLYMER

FIELD OF THE INVENTION

The present application relates to a personal care composition, and, more particularly, to a personal care composition comprising a conditioning, color protecting and/or styling copolymer for a keratin substrate of hair and/or skin origin.

BACKGROUND OF THE INVENTION

Undamaged virgin hair is smooth and shiny; its cuticles on the surface of the hair lie down smoothly making the combing easy. The hair surface is also hydrophobic in nature preventing excessive water absorption during washing. When the hair is either mechanically or chemically damaged through bleaching, perming or coloring, the hair surface becomes rough and frizzy and difficult to detangle and comb. As the hair surface becomes more hydrophilic, the resulting hair fibers swell during washing, making the hair even more difficult to comb.

Current conditioning and/or styling systems for regular and damaged hair generally use one or more combinations of cationic surfactants, amphoteric surfactants, silicones, fatty alcohols, polyquaterniums, amino acids, proteins, lipids and humectants. Wet conditioning of regular or damaged hair is accomplished by neutralizing the anionic charge of the hair by positively charged surfactants and polymers and creating a hydrophobic layer from surfactant and polymers. This hydrophobic layer results in a reduction of the swelling of the hair fibers by making the hair more hydrophobic and reducing friction of the hair fibers. An overall result of wet conditioning is improved detangling, manageability and soft feel of the hair. Upon treatment with cleansing systems like shampoos, 2in1 shampoos, body washes or shower gels, the combing performance, detangling properties, hydrophobicity of the hair and lubricity are not maintained sufficiently.

Further, fading of oxidative hair color is a common and frequent complaint of majority of the end-users, and wherein, the fading occurs because of our daily grooming products such as the shampoo, conditioning and styling and its associated grooming process therein. Such frequent shampoo and conditioning of hair substrate leads to significant color wash-out. The color fade occurred during hair wash is influenced by the cuticle damage of the hair, the shade of the hair color and the extent of exposure of hair to water during washing. Further, the more damage to the cuticle facilitates more color fading/leaching during hair wash, and therefore water has been determined to be responsible for most color loss during shampooing.

Accordingly, prevention of color fading/leaching is a very prominent requirement in the hair care market today. Many hair care products claim to prevent or capable of withstanding color fading of hair stresses up to certain amount of washes (e.g. up to 40 washes) or up to certain amount of time (e.g. up to 8 weeks). While many shampoos, conditioners and hair treatments has helped to prevent color fade, the best color protection products are leave-on products that need to be reapplied every time hair is washed. The rinse-off products are usually shampoo and conditioner regimens that need work together to provide adequate cleansing and conditioning to hair. Also, rinse-off products work better when used along with a leave-on product.

Further, the extent of duration for which the hair is exposed to water plays a key role in color fading; therefore, it is important to reduce said exposure duration spent in water based cleaning and conditioning of hair. The current application is designed to deliver color protection and conditioning specifically from rinse-off products.

United States Publication Number 20150297496 assigned to Hercules Incorporated discloses a personal care conditioning and/or styling composition for a keratin substrate comprising: (i) about 50 wt. % to 95 wt. % of at least one cationic or pseudo-cationic monomer selected from the group consisting of acrylamidopropyl trimethylammonium chloride (APTAC) and/or Vinylpyrrolidone (VP); (ii) about 1 wt. % to 30 wt. % of at least one anionic monomer selected from the group consisting of (a) acrylic acid (AA), (b) acrylamido methylpropyl sulfonate (AMPS), and/or (c) sodium methyl allyl sulfonate (SMAS); and (iii) about 0.1 wt. % to 20 wt. % of at least one hydrophobic monomer selected from the group consisting of (a) polyoxyethylene (PEG)-18-behenylether-methacrylate (BEM) (b) Laurylethoxylated-methacrylate (LEM), (c) stearyl acrylate (SA), (d) Stream-10-allyl-ether, (e) Vinylcaprolactam (V-cap), and/or (f) Hydroxyethyl-pyrrolidone-methacrylate (M06). Also described is a process of preparing said polymer, and its method of use.

United States Publication Number 20110219552 assigned to ISP Investments Inc. discloses a method of protecting dyed hair color from fading or wash-out during exposure to air and/or shampooing is described. In accordance with one aspect the method includes treating dyed hair with a composition containing (i) a hydrophobically modified quaternary polymer, (ii) a hydrophobically modified polymer plus a cationic surfactant, (iii) a polymer containing diethylaminopropyl methacrylamide (DMAPMA), dimethylaminoethyl methacrylamide (DMAEMA) or diethylaminoethyl methacrylamide (DEAEMA) or (iv) a combination thereof.

Therefore, there is an increasing demand for hair care products designed to retain the properties of "virgin hair" and to prevent possible color fading during the cleansing, conditioning, chemical and mechanical treatment. In the present application, the limitations set forth above are addressed by a personal care conditioning, color-protecting and/or styling composition for a keratin substrate comprising: (A) at least one conditioning and/or styling ter/tetra polymer obtained from polymerizing: (i) about 0.1 wt. % to 99 wt. % of acrylamidopropyl trimethylammonium chloride (APTAC), a cationic monomer; (ii) about 0.1 wt. % to 30 wt. % of at least one anionic monomer selected from the group consisting of (a) acrylic acid (AA), (b) acrylamido methylpropyl sulfonate (AMPS), and/or (c) sodium methyl allyl sulfonate (SMAS); and (iii) about 0.1 wt. % to about 20 wt. % of methacryloylaminopropyl lauryl-dimethyl ammonium chloride (MAPLDMAC), a hydrophobically modified cationic monomer; (B) at least one cosmetically acceptable excipient; and (C) optionally, at least one effective amount of personal care active ingredient.

SUMMARY OF THE INVENTION

The present application provides a personal care conditioning, color-protecting and/or styling composition for a keratin substrate comprising: (A) at least one conditioning and/or styling ter/tetra polymer obtained from polymerizing: (i) about 0.1 wt. % to 99 wt. % of acrylamidopropyl trimethylammonium chloride (APTAC), a cationic monomer; (ii) about 0.1 wt. % to 30 wt. % of at least one anionic monomer selected from the group consisting of (a) acrylic acid (AA), (b) acrylamido methylpropyl sulfonate (AMPS), and/or (c) sodium methyl allyl sulfonate (SMAS); and (iii) about 0.1 wt. % to about 20 wt. % of methacryloylaminopropyl lauryl-dimethyl ammonium chloride (MAPLDMAC), a hydrophobically modified cationic monomer; (B) at least one cosmetically acceptable excipient; and (C) optionally, at least one effective amount of personal care active ingredient.

An important embodiment of the present application is to provide a personal care composition which is capable of fixing or treating hair conditioning, color-protecting and/or styling properties comprising detangling, wet combability, wet feel, dry combability, dry feel, sheen, static flyaway control, hydrophobicity, surface smoothening, improved deposition, no build-up, color protection or color fading, and/or curl retention. Moreover, the composition is able to provide "virgin feel condition" to the hair after multiple washes particularly with respect to (1) increased hydrophobicity, (2) improved detangling and wet combability, (3) improved deposition, and/or (4) no build-up.

Another important embodiment of the present application provides a method for treating or fixing regular or damaged keratin substrate comprising contacting said keratin substrate with an effective amount of personal care composition comprising: (A) a conditioning, color protecting and/or styling terpolymer of (i) about 50 wt. % to 99 wt. % of acrylamidopropyl trimethylammonium chloride (APTAC); (ii) about 0.1 wt. % to 30 wt. % of an anionic monomer selected from the group consisting of (a) acrylic acid (AA), (b) acrylamido methylpropyl sulfonate (AMPS) or (c) sodium methyl allyl sulfonate (SMAS); and (iii) about 0.1 wt. % to 20 wt. % of a hydrophobic monomer selected from the group consisting of (a) methacryloylaminopropyl lauryl-dimethyl ammonium chloride (MAPLDMAC), a hydrophobically modified cationic monomer; wherein said terpolymer has a cationic degree of substitution (Cat-DS) of greater than about 0.001 units, and wherein the cationic charge density is in the range of about 1 meq/g to about 6 meq/g.

Yet another embodiment of the present application provides a method for washing or caring a keratin substrate comprising applying an effective amount of composition comprising: (A) a conditioning and/or styling terpolymer of (i) about 50 wt. % to 99 wt. % of acrylamidopropyl trimethylammonium chloride (APTAC); (ii) about 0.1 wt. % to 30 wt. % of an anionic monomer selected from the group consisting of (a) acrylic acid (AA), (b) acrylamido methylpropyl sulfonate (AMPS) or (c) sodium methyl allyl sulfonate (SMAS); and (iii) about 0.1 wt. % to 20 wt. % of a hydrophobic monomer selected from the group consisting methacryloylaminopropyl lauryl-dimethyl ammonium chloride (MAPLDMAC), a hydrophobically modified cationic monomer; wherein said terpolymer has a cationic degree of substitution (Cat-DS) of greater than about 0.001 units, and wherein the cationic charge density is in the range of about 1 meq/g to about 6 meq/g.

Still another embodiment of the present application provides a process for preparing a conditioning, color protecting, and/or styling terpolymer comprising polymerizing: (i) about 50 wt. % to 99 wt. % of acrylamidopropyl trimethylammonium chloride (APTAC), a cationic monomer; (ii) about 0.1 wt. % to 30 wt. % of an anionic monomer selected from the group consisting of (a) acrylic acid (AA), (b) acrylamido methylpropyl sulfonate (AMPS) or (c) sodium methyl allyl sulfonate (SMAS); and (iii) about 0.1 wt. % to 20 wt. % of a methacryloylaminopropyl lauryl-dimethyl ammonium chloride (MAPLDMAC), a hydrophobically modified cationic monomer; wherein the prepared terpolymer has a cationic degree of substitution (Cat-DS) of greater than about 0.001 units, and wherein the cationic charge density is in the range of about 1 meq/g to about 6 meq/g.

One another embodiment of the present application provides a method of protecting dyed hair color from fading or wash-out during exposure to air and/or shampooing which comprising contacting/treating said dyed hair with an effective amount of personal care composition comprising: (A) a conditioning, color protecting and/or styling terpolymer of (i) about 50 wt. % to 99 wt. % of acrylamidopropyl trimethylammonium chloride (APTAC), a cationic monomer; (ii) about 0.1 wt. % to 30 wt. % of an anionic monomer selected from the group consisting of (a) acrylic acid (AA), (b) acrylamido methylpropyl sulfonate (AMPS) or (c) sodium methyl allyl sulfonate (SMAS); and (iii) about 0.1 wt. % to 20 wt. % of methacryloylaminopropyl lauryl-dimethyl ammonium chloride (MAPLDMAC), a hydrophobically modified cationic monomer; wherein said terpolymer has a cationic degree of substitution (Cat-DS) of greater than about 0.001 units, and wherein the cationic charge density is in the range of about 1 meq/g to about 6 meq/g.

BRIEF DESCRIPTION OF THE FIGURES

Further embodiments of the present invention can be understood with the appended figures.

FIG. 5 is a Hair characteristics Evaluation Sheet

DETAILED DESCRIPTION OF THE INVENTION

Figure 1:
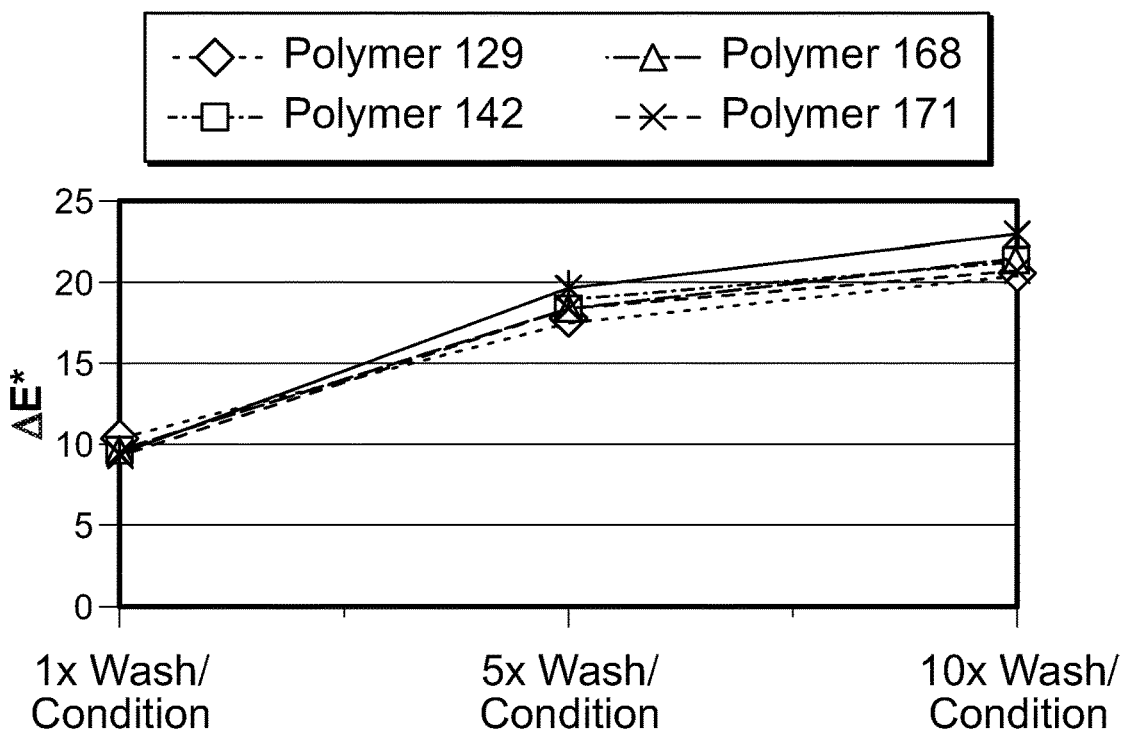
FIG. 1 is Summary of Color Protection data ($\Delta E^*$ measurement) with different monomer ratios.

While this specification concludes with claims particularly pointing out and distinctly claiming that which is regarded as the invention, it is anticipated that the invention can be more readily understood through reading the following detailed description of the invention and study of the included examples The singular forms "a," "an," and "the" include plural forms unless the context clearly dictates otherwise specified or clearly implied to the contrary by the context in which the reference is made. The term "Comprising" and "Comprises of" includes the more restrictive claims such as "Consisting essentially of" and "Consisting of".

The term "about" can indicate a difference of 10 percent of the value specified. Numerical ranges as used herein are meant to include every number and subset of numbers enclosed within that range, whether particularly disclosed or not. Further, these numerical ranges should be construed as providing support for a claim directed to any number or subset of numbers in that range.

All percentages, parts, proportions and ratios as used herein, are by weight of the total composition, unless otherwise specified. All such weights as they pertain to listed ingredients are based on the active level and, therefore; do not include solvents or by-products that may be included in commercially available materials, unless otherwise specified.

All references to singular characteristics or limitations of the present invention shall include the corresponding plural characteristic or limitation, and vice-versa, unless otherwise specified or clearly implied to the contrary by the context in which the reference is made.

As used herein, the words "preferred" or "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

References herein to "one embodiment" or "one aspect" or "one version" or "one objective" of the invention include one or more such embodiment, aspect, version or objective, unless the context clearly dictates otherwise.

All publications, articles, papers, patents, patent publications, and other references cited herein are hereby incorporated herein in their entirety for all purposes to the extent consistent with the disclosure herein.

The term "polymer" refers to a compound comprising repeating structural units (monomers) connected by covalent chemical bonds. Polymers may be further derivatized, cross-linked, grafted or end-capped. Non-limiting examples of polymers include copolymers, terpolymers, quaternary polymers, and homologues. The term "copolymer" refers to a polymer consisting essentially of two or more different types of monomers polymerized to obtain said copolymer, for example, a terpolymer or tetrapolymer and the like.

The term "conditioning agents", and grammatical variations thereof, as it relates to compositions for hair care includes cosmetically and pharmaceutically useful materials that can function as humectants, moisturizers, and emollients. It is recognized that some conditioning agents can serve more than one function in a composition, such as an emulsifying agent, a lubricant, and/or a solvent. Conditioning agents include any material which is used to give a particular conditioning benefit to hair. In hair treatment compositions, suitable conditioning agents are those which deliver one or more benefits relating to shine, softness, combability, antistatic properties, wet-handling, damage repair, manageability, detangling, body, and lubricity.

As used herein, the term "leave-on" is intended to mean a composition that is applied to and left on the hair for at least one hour until next cleansing. As used herein, the term "rinse-off" is intended to mean a composition that is applied to the hair and washed therefrom shortly after application.

The term "keratin substrate" as used herein includes skin, nails and "keratin fibers", and wherein the "keratin fibers" means hair on head, eyelashes, eyebrows and other mammalian bodily hair.

What is described herein is a personal care conditioning, color-protecting and/or styling composition for a keratin substrate comprising: (A) at least one conditioning and/or styling ter/tetra polymer obtained from polymerizing: (i) about 0.1 wt. % to 99 wt. % of acrylamidopropyl trimethylammonium chloride (APTAC), a cationic monomer; (ii) about 0.1 wt. % to 30 wt. % of at least one anionic monomer selected from the group consisting of (a) acrylic acid (AA), (b) acrylamido methylpropyl sulfonate (AMPS), and/or (c) sodium methyl allyl sulfonate (SMAS); and (iii) about 0.1 wt. % to about 20 wt. % of methacryloylaminopropyl lauryl-dimethyl ammonium chloride (MAPLDMAC), a hydrophobically modified cationic monomer; (B) at least one cosmetically acceptable excipient; and (C) optionally, at least one effective amount of personal care active ingredient.

In one embodiment, the range of cationic monomer (APTAC) for preparing a desired copolymer, terpolymer or tetra polymer of present application include but not limited to 50 wt. % to 55 wt. %; 56 wt. % to 60 wt. %; 61 wt. % to 65 wt. %; 66 wt. % to 70 wt. %; 71 wt. % to 75 wt. %; 76 wt. % to 80 wt. %; 81 wt. % to 85 wt. %; 86 wt. % to 90 wt. %; 91 wt. % to 95 wt. %.

According to another embodiment of the present application, the preferred range of an anionic monomer employed for preparing desired copolymer of present application includes but not limited to 1 wt. % to 5 wt. %; 6 wt. % to 10 wt. %; 11 wt. % to 15 wt. %; 16 wt. % to 20 wt. %; 21 wt. % to 25 wt. %; 26 wt. % to 30 wt. %.

The preferred range of a hydrophobically modified monomer employed for preparing a desired copolymer of present application includes but not limited to 0.01 wt. % to 5 wt. %; 6 wt. % to 10 wt. %; 11 wt. % to 15 wt. %; 16 wt. % to 20 wt. %.

The weight average molecular weight of said co/ter/tetra polymer of the present application, as determined by gel permeation chromatography (GPC), is at least about 10,000, preferably about 100,000 to about 2,000,000, more preferably from about 200,000 to about 500,000 g/mol, alternatively, viscometry can also be used to determine the average molecular weight of the present application.

The copolymer of use in the personal care composition of the invention has a cationic degree of substitution (Cat-DS) of greater than about 0.001 units. Preferably, the copolymer is a terpolymer or tetrapolymer having a cationic degree of substitution in the range of 0.001 to about 5.0, preferably in the range of from about 0.2 to about 3.0, more preferably in the range of about 0.4 to about 3.0.

A conditioning, color protecting and/or styling terpolymer/tetrapolymer of the present application is obtained by polymerizing: (i) about 50 wt. % to 99 wt. % of acrylamidopropyl trimethylammonium chloride (APTAC), a cationic monomer; (ii) about 0.1 wt. % to 30 wt. % of acrylamido methylpropyl sulfonate (AMPS), an anionic second monomer; and (iii) about 0.1 wt. % to 20 wt. % methaacryloylaminopropyl lauryl-dimethyl ammonium chloride (MAPLDMAC), a hydrophobically modified cationic monomer; wherein said terpolymer has a cationic degree of substitution (Cat-DS) of greater than about 0.001 units, and wherein the cationic charge density is in the range of about 1 meq/g to about 6 meq/g.

Non-limiting terpolymers or tetrapolymers of the present application include but are not limited to:

A. a terpolymer of (i) about 50 wt. % to 95 wt. % of acrylamidopropyl trimethylammonium chloride (APTAC), a cationic monomer; (ii) about 1 wt. % to 30 wt. % of acrylamido methylpropyl sulfonate (AMPS), an anionic monomer; and (iii) about 0.1 wt. % to 20 wt. % methaacryloylaminopropyl lauryl-dimethyl ammonium chloride (MAPLDMAC), a hydrophobically modified cationic monomer.

B. a terpolymer of (i) about 50 wt. % to 95 wt. % of acrylamidopropyl trimethylammonium chloride (APTAC), a cationic monomer; (ii) about 1 wt. % to 30 wt. % of sodium methyl allyl sulfonate (SMAS), an anionic monomer; and (iii) about 0.1 wt. % to 20 wt. % methaacryloylaminopropyl lauryl-dimethyl ammonium chloride (MAPLDMAC), a hydrophobically modified cationic monomer.

C. a terpolymer of (i) about 50 wt. % to 95 wt. % of acrylamidopropyl trimethylammonium chloride (APTAC), a cationic monomer; (ii) about 1 wt. % to 30 wt. % of acrylic acid (AA), an anionic monomer; and (iii) about 0.1 wt. % to 20 wt. % methaacryloylaminopropyl lauryl-dimethyl ammonium chloride (MAPLDMAC), a hydrophobically modified cationic monomer.

D. a tetrapolymer of (i) about 50 wt. % to 95 wt. % of acrylic acidamidopropyl trimethylammonium chloride (APTAC), a cationic monomer; (ii) about 1 wt. % to 30 wt. % of acrylamido methylpropyl sulfonate (AMPS), an anionic monomer; (iii) about 0.1 wt. % to 20 wt. % methaacryloylaminopropyl lauryl-dimethyl ammonium chloride (MAPLDMAC), a hydrophobically modified cationic monomer; and (iv) about 0.1 wt. % to 20 wt. % vinylcaprolactam (V-cap), a hydrophobic monomer.

E. a tetrapolymer of (i) about 50 wt. % to 95 wt. % of acrylic acidamidopropyl trimethylammonium chloride (APTAC), a cationic monomer; (ii) about 1 wt. % to 30 wt. % of acrylamido methylpropyl sulfonate (AMPS), an anionic monomer; (iii) about 0.1 wt. % to 20 wt. % methaacryloylaminopropyl lauryl-dimethyl ammonium chloride (MAPLDMAC), a hydrophobically modified cationic monomer; and (iv) about 50 wt. % to 95 wt. % of Vinylpyrrolidone (VP), a pseudo-cationic monomer.

According to one important embodiment of the present application it is contemplated to select at least one cationic monomer for the hydrophobic modification to produce desired hydrophobically modified cationic monomers for the present application. Such cationic monomer would include but not limited to acrylic acidamidopropyl trimethylammonium chloride (APTAC), diallyldimethyl ammonium chloride (DADMAC), 3-methacrylamidopropyltrimethylammonium chloride (MAPTAC), 2-methacrylatoethyltrimethylammonium chloride (METAC), 2-acryloxyethyl trimethyl ammonium chloride (AETAC), diallyldimethyl ammonium bromide, diallyldimethyl ammonium sulfate, diallyldimethyl ammonium phosphates, dimethallyldimethyl ammonium chloride, diethylallyl dimethyl ammonium chloride, diallyl di(beta-hydroxyethyl) ammonium chloride, or diallyl di(beta-ethoxyethyl) ammonium chloride.

In one another embodiment of the present application, it is contemplated to employ at least one cationic monomer selected from the group including but not limited to acrylic acidamidopropyl trimethylammonium chloride (APTAC), diallyldimethyl ammonium chloride (DADMAC), 3-methacrylamidopropyltrimethylammonium chloride (MAPTAC), 2-methacrylatoethyltrimethylammonium chloride (METAC), 2-acryloxyethyl trimethyl ammonium chloride (AETAC), diallyldimethyl ammonium bromide, diallyldimethyl ammonium sulfate, diallyldimethyl ammonium phosphates, dimethallyldimethyl ammonium chloride, diethylallyl dimethyl ammonium chloride, diallyl di(beta-hydroxyethyl) ammonium chloride, or diallyl di(beta-ethoxyethyl) ammonium chloride, and wherein, hydrophobically modified cationic monomer is generated by employing following non-limiting hydrophobic functional groups including styrene, vinyl esters of a $C_2$ to $C_{18}$ carboxylic acid and N-vinyl amides of a $C_2$ to $C_{18}$ carboxylic acid, substituted acrylic acids, substituted acrylamides, esters of (meth)acrylic acid, (meth)acrylonitrile, esters of unsaturated polyfunctional acids and vinyl esters of $C_2$ to $C_{18}$ carboxylic acids. For suitable hydrophobic functional groups for preparing modified cationic monomer are disclosed in published U.S. Pat. Nos. 7,659,354, 8,287,657, and 9,080,129.

A process for preparing a conditioning, color protecting, and/or styling terpolymer comprising polymerizing: (i) about 50 wt. % to 99 wt. % of acrylamidopropyl trimethylammonium chloride (APTAC), a cationic monomer; (ii) about 0.1 wt. % to 30 wt. % of an anionic monomer selected from the group consisting of (a) acrylic acid (AA), (b) acrylamido methylpropyl sulfonate (AMPS) or (c) sodium methyl allyl sulfonate (SMAS); and (iii) about 0.1 wt. % to 20 wt. % of a methacryloylaminopropyl lauryl-dimethyl ammonium chloride (MAPLDMAC), a hydrophobically modified cationic monomer; wherein the prepared terpolymer has a cationic degree of substitution (Cat-DS) of greater than about 0.001 units, and wherein the cationic charge density is in the range of about 1 meq/g to about 6 meq/g.

According to one important aspect of the present application, the above disclosed copolymers, terpolymers and tetrapolymers of the present application can advantageously be combined and formulated with (1) at least one anionic, cationic, nonionic and/or zwitter-ionic/amphoteric polymers or mixtures thereof, (2) at least one personal care active ingredient, and/or (3) at least one cosmetically acceptable excipient.

The cationic polymers that can be used along with conditioning, color protecting, and/or styling copolymer of this application are those known to improve the cosmetic properties of hair which may be normal or damaged in nature. The expression "cationic polymer" as used herein, indicates any polymer containing cationic groups and/or ionizable groups in cationic groups. The cationic polymers used generally have a molecular weight the average number of which falls between about 500 and 5,000,000 and preferably between 1000 and 3,000,000. The preferred cationic polymers are chosen from among those containing units including primary, secondary, tertiary, and/or quaternary amine groups that may either form part of the main polymer chain or a side chain. Useful cationic polymers include known polyamine, polyaminoamide, and quaternary polyammonium types of polymers, such as: (1) Homopolymers and copolymers derived from acrylic or methacrylic esters or amides. The copolymers can contain one or more units derived from acrylamides, methacrylamides, diacetone acrylamides, acrylamides and methacrylamides, acrylic or methacrylic acids or their esters, vinyllactams such as vinyl pyrrolidone or vinyl caprolactam, and vinyl esters. (2) Derivatives of cellulose ethers containing quaternary ammonium groups, such as hydroxy ethyl cellulose quaternary ammonium that has reacted with an epoxide substituted by a trimethyl ammonium group. (3) Derivatives of cationic cellulose such as cellulose copolymers or derivatives of cellulose grafted with a hydrosoluble quaternary ammonium monomer, as described in U.S. Pat. No. 4,131,576, such as the hydroxy alkyl cellulose, and the hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium. (4) Cationic polysaccharides such as described in U.S. Pat. Nos. 3,589,578 and 4,031,307, guar gums containing cationic trialkyl ammonium groups, guar gums modified by a salt, e.g., chloride of 2,3-epoxy propyl trimethyl ammonium, Cassia, Chitosan, Chitin and the like. (5) Polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers. (6) Water-soluble polyamino amides prepared by polycondensation of an acid compound with a polyamine. These polyamino amides may be reticulated. (7) Derivatives of polyamino amides resulting from the condensation of polyalcoylene polyamines with polycarboxylic acids followed by alcoylation by bi-functional agents. (8) Polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers are described in U.S. Pat. Nos. 3,227,615 and 2,961,347. (9) The cyclopolymers of alkyl dialyl amine or dialkyl diallyl ammonium such as the homopolymer of dimethyl diallyl ammonium chloride and copolymers of diallyl dimethyl ammonium chloride and acrylamide. (10) Quaternary diammonium polymers such as hexadimethrine chloride. Polymers of this type are described particularly in U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945, and 4,027,020. (11) Quaternary polyammonium polymers, including, for example, Mirapol® A 15, Mirapol® AD1, Mirapol® AZ1, and Mirapol® 175 products sold by Miranol. (12) The quaternary polymers of vinyl pyrrolidone and vinyl imidazole such as the products sold under the names Luviquat® FC 905, FC550, and FC 370 by BASF. (13) Quaternary polyamines (14) Reticulated polymers known in the art.

Suitable Polyquaternium type of cationic polymers for the present application would include but not limited to Polyquaternium 4, Polyquaternium 5, Polyquaternium 6, Polyquaternium 7, Polyquaternium 10, Polyquaternium 11, Polyquaternium 15, Polyquaternium 16, Polyquaternium 22, Polyquaternium 28, Polyquaternium 32, Polyquaternium 37, Polyquaternium 39, Polyquaternium 46, Polyquaternium 47, Polyquaternium 53, Polyquaternium 55, Polyquaternium 67, and/or Polyquaternium 87. Other polymers known by their CTFA category name "Quaternium" are suitable for the present application would include but not limited to Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

Other cationic polymers that may be used within the context of the invention are cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

The anionic polymers that can be employed along with a conditioning, color protecting, and/or styling copolymer of this application would include but are not limited to carboxylic acids such as acrylic acid (AA), methacrylic acid (MAA), 2-acrylamido-2-methylpropanesulfonic acid (AMPS), crotonic acid, styrene sulfonic acid, itconic acid, and the like.

Preferred anionic homo and copolymer of the present application would include but are not limited to (a) Homo- or copolymers of acrylic or methacrylic acid or salts thereof; (b) Copolymers of acrylic or methacrylic acids with a mono-ethylenic monomer; (c) Copolymers comprising: (i) one or more maleic, fumaric or itaconic acids or anhydrides and (ii) at least one monomer selected from vinyl esters, vinyl ethers, vinyl halides, phenylvinyl derivatives, acrylic acid and its esters, the anhydride functions of these copolymers optionally being monoesterified or monoamidated; (d) Copolymers comprising: (i) one or more maleic, citraconic or itaconic anhydrides and (ii) one or more monomers selected from allylic or methallylic esters optionally containing one or more acrylamide, methacrylamide, alpha-olefin, acrylic or methacrylic ester, acrylic or methacrylic acid or vinylpyrrolidone groups in their chain, the anhydride functions of these copolymers optionally being monoesterified or monoamidated; (e) Polyacrylamides containing carboxylate groups; (f) The polymers comprising sulphonic groups are polymers containing vinylsulphonic, styrenesulphonic, naphthalenesulphonic or acrylamidoalkylsulphonic units.

The amphoteric polymers cab be selected from the following polymers: (1) Polymers resulting from the copolymerization of a monomer derived from a vinyl compound bearing a carboxylic group such as, more particularly, acrylic acid, methacrylic acid, maleic acid, alpha-chloroacrylic acid, and a basic monomer derived from a substituted vinyl compound containing at least one basic atom, such as, more particularly, dialkylaminoalkyl methacrylate and acrylate, dialkylaminoalkylmethacrylamides and acrylamides. (2) Polymers containing units derived from: a) at least one monomer selected from acrylamides and methacrylamides substituted on the nitrogen with an alkyl radical, b) at least one acidic comonomer containing one or more reactive carboxylic groups, and c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

Nonionic polymers having at least one fatty chain and at least one hydrophilic unit, are preferably chosen from: (1) celluloses modified with groups containing at least one fatty chain such as, for example: hydroxyethyl celluloses modified with groups containing at least one fatty chain such as alkyl, arylalkyl or alkylaryl groups or mixtures thereof, and in which the alkyl groups are preferably $C_8$-$C_{22}$; (2) hydroxypropyl guars modified with groups containing at least one fatty chain; (3) polyether urethanes containing at least one fatty chain such as a $C_8$-$C_{30}$ alkyl or alkenyl group; (4) copolymers of $C_1$-$C_6$ alkyl methacrylates or acrylates and of amphiphilic monomers comprising at least one fatty chain; (5) copolymers of hydrophilic methacrylates or acrylates and of hydrophobic monomers comprising at least one fatty chain; (6) polyurethane polyethers comprising in their chain both hydrophilic blocks usually of polyoxyethylenated nature and hydrophobic blocks which may be aliphatic sequences alone and/or cycloaliphatic and/or aromatic sequences; and (7) polymers with an aminoplast ether backbone containing at least one fatty chain. Other relevant nonionic polymers which are disclosed in US Patent Application No's. 20070134191 and 20110165108 may be employed for the purposes of the present application.

The polymerization of the polymer useful herein is carried out by any appropriate method known in the prior art by a person skilled in the art. Particularly, the polymerization is carried out by any one of the methods disclosed in "*Principles of Polymerization*" $4^{th}$ edition, 2004, Wiley by George Odian and is referred and disclosed herein in its entirety. Further, the polymerization of terpolymer of the present application may contain a suitable catalyst or initiators such as amines, bases, organic acids and/or photo-initiators. However, the preferred polymerization technique employed to prepare a conditioning polymer would include but not limited to radical polymerization, emulsion polymerization, ionic chain polymerization, bulk polymerization, suspension polymerization or precipitation polymerization.

It is contemplated to employ at least one personal care active ingredient for preparing a personal care composition of the present application comprising a conditioner, styling, and color-protecting polymer and at least one cosmetically acceptable agent, wherein, the preferred personal care active ingredient of the present application would include but not limited to Carnitine, Betain Aminoacids as i.e. valine, glycine, arginine, allantoin, tocopherol nicotinate, niacinamide, retinyl propionate, palmitoyl-gly-his-lys, phytosterol, polyphenolic compounds, flavonoids, flavones, flavonols, isoflavone, dexpanthenol, panthenol, bisabolol, farnesol, phytantriol, salicylic acid, zinc/sodium pyridinethione salts, piroctone olamine, selenium disulfide, tetrahydrocurcumin, glucosamine, N-acteyl glucosamine, vitamin B3, retinoids, peptides, phytosterol, dialkanoyl hydroxyproline, hexamidine, salicylic acid, N-acyl amino acids, escolols, sunscreen actives, UV-A/UV-B protecting agent, UV filters, water soluble vitamins, oil soluble vitamins, hesperedin, mustard seed extract, glycyrrhizic acid, glycyrrhetinic acid, carnosine, Butylated Hydroxytoluene (BHT) and Butylated Hydroxyanisole (BHA), ergothioneine, vanillin, vanillin derivatives, diethylhexyl syrinylidene malonate, melanostatine, sterol esters, fatty acids, poly-unsaturated fatty acids, anti-fungal agents, thiol compounds, N-acetyl cysteine, glutathione, thioglycolate, β-carotene, ubiquinone, amino acids, idebenone, dehydroacetic acid, Licohalcone A, creatine, creatinine, feverfew extract, yeast extract, beta glucans, alpha glucans, alone or in combination.

The effective amount of personal care active ingredient employed in the present application is in the range of from about 0.01 wt. % to about 10 wt. %, preferably about 0.1 wt. % to about 5.0 wt. % and more preferably in the range of 0.05 wt. % to about 3.0 wt. % of the total composition.

The personal care composition of present application is capable of fixing or treating hair and features conditioning and/or styling properties such as detangling, wet combability, wet feel, dry combability, dry feel, sheen, static flyaway control, hydrophobicity, surface smoothening, improved deposition, no build-up, color protection, and/or curl retention. Further, the personal care composition comprising a terpolymer of present application is able to provide "virgin feel condition" to the hair after multiple washes.

The personal care composition of present application can be an appropriate product selected from the group consisting of hair-care products, shampoos, hair conditioners, 2 in 1 shampoos, leave in and rinse off conditioners, hair treatments including intensive treatments, styling and treating hair compositions, hair perming products, hair straightners, hair relaxants, hair sprays and lacquers, permanent hair dyeing systems, hair styling mousses, hair gels, semi-permanent hair dyeing systems, temporary hair dyeing systems, hair bleaching agents, permanent hair wave systems, hair setting formulations, non-coloring hair preparations, hair-frizz-control gels, hair leave-in conditioners, hair pomades, hair de-tangling products, hair fixatives, hair conditioning mists, hair care pump sprays and other non-aerosol sprays, skin-care products, hair cuticle coats, skin care moisturizing mists, skin wipes, pore skin wipes, pore cleaners, blemish reducers, skin exfoliators, skin desquamation enhancers, skin towelettes, skin protection ointments, skin powders, skin pads, paste masks and muds, face masks, facial cleansing products, anti-acne preparations, bath products, shower products, liquid soaps, bar soaps, body oils, body lotions, body gels, body and hand preparations, face and body washes, bath salts, bath and body milks, foam baths, synthetic and non-synthetic soap bars, hand liquids, shaving lotions, shaving and aftershave preparations, pre-shaves and pre-electric shaves, nail varnishes, nail polish, nail polish remover, nail creams and lotions, cuticle softeners, nail conditioners, eye shadows, mascaras, eye liners, eye shadows, blushes, makeup, eye shadow sticks, baby lotions, baby baths and shampoos, baby conditioners, fragrances and/or odoriferous ingredients consisting preparations, dentifrices, deodorizing and antiperspirant preparations, decorative preparations, light protection formulations, treatment creams, lipsticks, dry and moist make-up, rouge, powders, depilatory agents, sun care products, compositions comprising UV blockers or UV protectors, anti-aging products, foundations, face powders, moisturizing preparations, tanning preparations, nose strips, make-up removers, cold creams, mousses, shower gels, personal care rinse-off products, gels, scrubbing cleansers, astringents, lip balms, lip glosses, anhydrous creams and lotions, oil/water, water/oil, multiple and macro and micro emulsions, water-resistant creams and lotions, mouth-washes, massage oils, toothpastes, clear gels and sticks, ointment bases, topical wound-healing products, aerosol talc, barrier sprays, vitamin, herbal-extract preparations, and/or controlled-release personal care products.

The personal care composition of present invention can be formulated in several required forms according to their necessity, and the non-limiting forms include emulsion, lotion, gel, vesicle dispersion, paste, cream, solid stick, mousse, shampoo, spray, balm, wipe, milk, foam, jellies, liquid, tonics, and/or enamel.

As used herein, the term "cosmetically acceptable excipient" means any ingredient/compound or mixture of ingredients/compounds or compositions that are typically employed to produce other desirable effects in personal care compositions. The preferred cosmetically acceptable excipients include but not limited to preservatives, antioxidants, chelating agents, sunscreen agents, proteins, amino acids, vitamins, dyes, hair coloring agents, plant extracts, plant derivatives, plant tissue extracts, plant seed extracts, plant oils, botanicals, botanical extracts, humectants, fragrances, perfumes, oils, emollients, lubricants, butters, penetrants, thickeners, viscosity modifiers, thickeners, polymers, resins, hair fixatives, film formers, surfactants, detergents, emulsifiers, opacifying agents, volatiles, propellants, liquid vehicles, carriers, salts, pH adjusting agents, neutralizing agents, buffers, hair conditioning agents, anti-static agents, anti-frizz agents, anti-dandruff agents, hair waving agents, hair straightening agents, relaxers, absorbents, fatty substances, gelling agents, moisturizers, hydrophilic or lipophilic active agent, preserving agents, fillers, dyestuffs, reducing agents, cosmetic oils, perfumes, liquid vehicles, solvents, carriers, silicones, and combinations thereof.

Suitable rheology modifiers and thickeners include synthetic and semi-synthetic rheology modifiers. Exemplary synthetic rheology modifiers include acrylic based polymers and copolymers. One class of acrylic based rheology modifiers are the carboxyl functional alkali-swellable and alkali-soluble thickeners (ASTs) produced by the free-radical polymerization of acrylic acid alone or in combination with other ethylenically unsaturated monomers. The polymers can be synthesized by solvent/precipitation as well as emulsion polymerization techniques. Exemplary synthetic rheology modifiers of this class include homopolymers of acrylic acid or methacrylic acid and copolymers polymerized from one or more monomers of acrylic acid, substituted acrylic acid, and salts and $C_1$-$C_{30}$ alkyl esters of acrylic acid and substituted acrylic acid. As defined herein, the substituted acrylic acid contains a substituent positioned on the alpha and/or beta carbon atom of the molecule wherein the substituent is preferably and independently selected from $C_{1-4}$ alkyl, —CN, and —COOH. Optionally, other ethylenically unsaturated monomers such as, for example, styrene, vinyl acetate, ethylene, butadiene, acrylonitrile, as well as mixtures thereof can be copolymerized into the backbone. The foregoing polymers are optionally crosslinked by a monomer that contains two or more moieties that contain ethylenic unsaturation. In one aspect, the crosslinker is selected from a polyalkenyl polyether of a polyhydric alcohol containing at least two alkenyl ether groups per molecule. Other Exemplary crosslinkers are selected from allyl ethers of sucrose and allyl ethers of pentaerythritol, and mixtures thereof. These polymers are more fully described in U.S. Pat. Nos. 5,087,445; 4,509,949; and 2,798,053 herein incorporated by reference in its entirety.

Another class of synthetic rheology modifiers and thickeners suitable for use in accordance with an embodiment of the present invention includes hydrophobically modified ASTs commonly referred to as hydrophobically modified alkali-swellable and alkali-soluble emulsion (HASE) polymers. Typical HASE polymers are free radical addition polymers polymerized from pH sensitive or hydrophilic monomers (e.g., acrylic acid and/or methacrylic acid), hydrophobic monomers (e.g., $C_1$-$C_{30}$ alkyl esters of acrylic acid and/or methacrylic acid, acrylonitrile, styrene), an "associative monomer", and an optional crosslinking monomer. The associative monomer comprises an ethylenically unsaturated polymerizable end group, a non-ionic hydrophilic midsection that is terminated by a hydrophobic end group. The non-ionic hydrophilic midsection comprises a polyoxyalkylene group, e.g., polyethylene oxide, polypropylene oxide, or mixtures of polyethylene oxide/polypropylene oxide segments. The terminal hydrophobic end group is typically a $C_8$-$C_{40}$ aliphatic moiety. Exemplary aliphatic moieties are selected from linear and branched alkyl substituents, linear and branched alkenyl substituents, carbocyclic substituents, aryl substituents, aralkyl substituents, arylalkyl substituents, and alkylaryl substituents. In one aspect, associative monomers can be prepared by the condensation (e.g., esterification or etherification) of a polyethoxylated and/or polypropoxylated aliphatic alcohol (typically containing a branched or unbranched $C_8$-$C_{40}$ aliphatic moiety) with an ethylenically unsaturated monomer containing a carboxylic acid group (e.g., acrylic acid, methacrylic acid), an unsaturated cyclic anhydride monomer (e.g., maleic anhydride, itaconic anhydride, citraconic anhydride), a monoethylenically unsaturated monoisocyanate (e.g., α,α-dimethyl-m-isopropenyl benzyl isocyanate) or an ethylenically unsaturated monomer containing a hydroxyl group (e.g., vinyl alcohol, allyl alcohol). Polyethoxylated and/or polypropoxylated aliphatic alcohols are ethylene oxide and/or propylene oxide adducts of a monoalcohol containing the $C_8$-$C_{40}$ aliphatic moiety. Non-limiting examples of alcohols containing a $C_8$-$C_{40}$ aliphatic moiety are capryl alcohol, iso-octyl alcohol (2-ethyl hexanol), pelargonic alcohol (1-nonanol), decyl alcohol, lauryl alcohol, myristyl alcohol, cetyl alcohol, cetyl alcohol, cetearyl alcohol (mixture of $C_{16}$-$C_{18}$ monoalcohols), stearyl alcohol, isostearyl alcohol, elaidyl alcohol, oleyl alcohol, arachidyl alcohol, behenyl alcohol, lignoceryl alcohol, ceryl alcohol, montanyl alcohol, melissyl, lacceryl alcohol, geddyl alcohol, and $C_2$-$C_{20}$ alkyl substituted phenols (e.g., nonyl phenol), and the like.

Another class of synthetic and semi-synthetic rheology modifiers and thickeners suitable for use in accordance with an embodiment of the present invention includes cationically modified acrylic polymers and copolymers and cationically modified cellulose ethers. The acrylic polymers and copolymers and cellulose ethers are cationically modified via quaternization. For the acrylic polymers and copolymers, quaternization can occur by polymerizing a quaternized monomer into the acrylic polymer backbone or by post functionalizing the acrylic polymer with a quaternizing agent.

Suitable surfactants or surfactant systems for preparing a personal care composition comprising a conditioning, color protecting, and/or styling copolymer of the present application can be selected from anionic, non-ionic, amphoteric, cationic and mixtures thereof. The contemplated surfactants for the present application are duly disclosed in PCT Publication Number WO 2014/071354 assigned to Hercules Incorporated, and it is considered in its entirety for the purposes of this application.

Suitable emulsifiers include the following classes of ethers and esters: ethers of polyglycols and of fatty alcohols, esters of polyglycols and of fatty acids, ethers of polyglycols and of fatty alcohols which are glycosylated, esters of polyglycols and of fatty acids which are glycosylated, ethers of $C_{12-30}$ alcohols and of glycerol or of polyglycerol, esters of $C_{12-30}$ fatty acids and of glycerol or of polyglycerol, ethers of oxyalkylene-modified $C_{12-30}$ alcohols and of glycerol or polyglycerol, ethers of $C_{12-30}$ fatty alcohols comprising and of sucrose or of glucose, esters of sucrose and of $C_{12-30}$ fatty acids, esters of pentaerythritol and of $C_{12-30}$ fatty acids, esters of sorbitol and/or of sorbitan and of $C_{12-30}$ fatty acids, ethers of sorbitol and/or of sorbitan and of alkoxylated sorbitan, ethers of polyglycols and of cholesterol, esters of $C_{12-30}$ fatty acids and of alkoxylated ethers of sorbitol and/or sorbitan, and combinations thereof. Linear or branched type silicone emulsifiers may also be used.

The personal care composition of present application can be preserved by adding minor quantity of preservatives to the compositions. Such preservatives can be selected from, but are not limited to triazoles, imidazoles, naphthalene derivatives, benzimidazoles, morphline derivatives, dithiocarbamates, benzisothiazoles, benzamides, boron compounds, formaldehyde donors, isothiazolones, thiocyanates, quaternary ammonium compounds, iodine derivates, phenol derivatives, micobicides, pyridines, dialkylthiocarbamates, nitriles, parabens, alkyl parabens and salts thereof.

Suitable antioxidants may be added to facilitate the enhanced shelf-life of the personal care composition. Exemplary antioxidants that can be used include vitamins such as vitamin E, vitamin E acetate, vitamin C, vitamin A, and vitamin D, and derivatives thereof. Additional exemplary antioxidants include but are not limited to propyl, octyl and dodecyl esters of gallic acid, butylated hydroxyanisole (BHA), butylated hydroxytoluene (BHT), and nordihydroguaiaretic acid. In general, the required amount of antioxidant for the present composition is in the range of about 0.2 wt. % to about 2 wt. %, and can be provided in an amount of about 0.5 wt. % to about 1.5 wt. %, based on the total weight of the composition.

The preferred fatty substance based excipient for the present application include fatty alcohols, natural and synthetic waxes, ceramides, mineral oils, vegetable oils, animal oils, synthetic oils. The other preferred fatty substance are isododecane, hydrogenated polyisobutene, squalane, isononyl isononanoate, cyclotetra- and -pentadimethicones, phenyltrimethicone, ethylene homopolymers, ethoxylated fats and oils, fluoroalkanes, seracite, shea butter, arachidyl propionate alone or in combination. For the definition of waxes, mention may be made, for example, of P. D. Dorgan, Drug and Cosmetic Industry, December 1983, pp. 30-33.

The preferred waxes of the present application would include microcrystalline waxes, carnauba wax, candelilla wax, esparto wax, paraffin wax, ozokerite. It is also considered to use plant waxes such as olive tree wax, rice wax, fruit waxes, hydrogenated jojoba wax or the absolute waxes of flowers such as the essential wax of blackcurrant flower sold by the company Bertin (France), animal waxes such as beeswaxes, or modified beeswaxes; other waxes or waxy starting materials which can be used according to this application are, in particular, marine waxes and polyethylene waxes or polyolefins.

The animal or plant oils are preferably chosen from sunflower oil, corn oil, soybean oil, avocado oil, jojoba oil, marrow oil, Argan oil, grapeseed oil, sesame oil, hazelnut oil, fish oils, glyceryl tricaprocaprylate, or plant or animal oils of formula $R_1COOR_2$ in which $R_1$ represents a higher fatty acid residue containing from 7 to 29 carbon atoms and $R_2$ represents a linear or branched hydrocarbon-based chain containing from 3 to 30 carbon atoms, particularly alkyl or alkenyl, for example purcellin oil or liquid jojoba wax. Further, it is also possible to use natural or synthetic essential oils such as, for example, eucalyptus oil, lavandin oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, cade oil, almond oil, argan oil, avocado oil, olive oil, sun flower oil, cedar oil, wheat germ oil and bergamot oil.

Moisturizers employed in the present invention would include glycols, glycerols, propylene glycol, diethylene glycol monoethyl ether, sorbitol, sodium salt of pyroglutamic acid, glycerol, glycerol derivatives, glycerin, trehalose, sorbitol, maltitol, dipropylene glycol, 1,3-butylene glycol, sodium hyaluronate, and the like. Examples of humectants which can be incorporated into a product of the present application are glycerine, propylene glycol, polypropylene glycol, polyethylene glycol, lactic acid, sodium lactate, pyrrolidone carboxylic acid, urea, phospholipids, collagen, elastin, ceramides, lecithin sorbitol, PEG-4, and mixtures thereof. Additional suitable moisturizers are polymeric moisturizers that belong to water soluble and/or water swellable in nature. Polysaccharides such as hyaluronic acid, chitosan can also be employed along with moisturizers of the present application as binder to enhance their property.

The preferred solvent of the present application may consist of water, a cosmetically acceptable solvent, or a blend of water and a cosmetically acceptable solvent, such as a lower alcohol composed of $C_1$ to $C_4$, such as ethanol, isopropanol, t-butanol, n-butanol, alkylene glycols such as propylene glycol, and glycol ethers. However, the compositions of the invention can be anhydrous. The most preferred solvents of the present application would include water, ethanol and/or iso-propanol.

It is contemplated to employ other suitable solvents for preparing products of the present application which would include but are not limited to, linear and branched $C_1$-$C_6$ alcohols, such as ethanol, propanol, isopropanol, butanol, hexanol, and mixtures thereof; aromatic alcohols, such as benzyl alcohol, cycloaliphatic alcohols, such as cyclohexanol, and the like; saturated $C_{12}$-$C_{30}$ fatty alcohol, such as lauryl alcohol, myristyl alcohol, cetyl alcohol, stearyl alcohol, behenyl alcohol, and the like. Non-limiting examples of polyols include polyhydroxy alcohols, such as glycerin, propylene glycol, butylene glycol, hexylene glycol, $C_2$-$C_4$ alkoxylated alcohols and $C_2$-$C_4$ alkoxylated polyols, such as ethoxylated, propoxylated, and butoxylated ethers of alcohols, diols, and polyols having about 2 to about 30 carbon atoms and 1 to about 40 alkoxy units, polypropylene glycol, polybutylene glycol, and the like. Non-limiting examples of non-aqueous auxiliary solvents include silicones, and silicone derivatives, such as cyclomethicone, and the like, aliphatic solvents such as cyclohexane and heptane, ketones such as acetone and methyl ethyl ketone, and mixtures thereof; ethers such as diethyl ether, dimethoxymethane, and mixtures thereof, natural and synthetic oils and waxes, such as vegetable oils, plant oils, animal oils, essential oils, mineral oils, $C_7$-$C_{40}$ isoparaffins, alkyl carboxylic esters, such as ethyl acetate, amyl acetate, ethyl lactate, and the like, jojoba oil, shark liver oil, and the like.

The preferred neutralizing agents that can be included in the product of the present application to neutralize components such as e.g. an emulsifier or a foam builder/stabilizer include but are not limited to alkali hydroxides such as a sodium and potassium hydroxide; organic bases such as methylethylamine (MEA), ammonia, aminoalcohols, lithium hydroxide, diethanolamine (DEA); triethanolamine (TEA), aminomethyl propanol, and mixtures thereof; amino acids such as arginine and lysine and any combination of any foregoing. The neutralizing agent can be present in an amount of about 0.01 wt. % to about 8 wt. %, preferably, 1 wt. % to about 5 wt. %.

Other preferred pH adjusting agents would include alkaline pH adjusting agents include alkali metal hydroxides, such as sodium hydroxide, and potassium hydroxide; ammonium hydroxide; organic bases, such as triethanolamine, diisopropylamine, dodecylamine, diisopropanolamine, aminomethyl propanol, cocamine, oleamine, morpholine, triamylamine, triethylamine, tromethamine (2-amino-2-hydroxymethyl)-1,3-propanediol), and tetrakis(hydroxypropyl)ethylenediamine; and alkali metal salts of inorganic acids, such as sodium borate (borax), sodium phosphate, sodium pyrophosphate, and the like, and mixtures thereof. Acidic pH adjusting agents can be organic acids, including amino acids, and inorganic mineral acids. Non-limiting examples of acidic pH adjusting agents include acetic acid, citric acid, fumaric acid, glutamic acid, glycolic acid, hydrochloric acid, lactic acid, nitric acid, phosphoric acid, sodium bisulfate, sulfuric acid, tartaric acid, and the like, and mixtures thereof. The desired pH of the personal care composition is in the range of from about 3 to about 13, and in some embodiment, it is preferably between about 4 to about 8. The utility levels of the pH modifying agent may be present in an effective amount required to achieve the desired pH level.

Examples of anti-dandruff agents that can be used are cimbazole, octopirox and zinc pyrithione, salicylic acid, elemental sulfur, selenium dioxide, and the azole antimycotics.

According to one important embodiment of the present application, it is contemplated to employ natural plant extracts showing hair conditioning, restructuring effects, growing effects, can be used in the conditioners. Those are preferably the extracts from almond, coconut, mango, peach, lemon, wheat, rosemary, apricot, algae, grapefruit, sandalwood, lime orange, *Acacia concinna, Butea parviflora, Butea superb, Butea frondosa* and/or *Aloe Vera*. The extracts of these plants are obtained from seeds, roots, stem, leaves, flowers, bark, fruits, and/or whole plant.

According to one important embodiment of the present application, it is contemplated to employ at least one organic UV filters which can filter out UV rays can be selected from hydrosoluble or liposoluble filters, whether siliconated or nonsiliconated, and mineral oxide particles, the surface of which may be treated. The detailed UV filters that are considered for the present application are duly disclosed in PCT Publication Number WO 2014/071354 assigned to Hercules Incorporated. However, the Preferred UV filters include Escalol HP-610 (dimethylpabamido propyl laurdimonium tosylate and propylene glycol stearate) and Crodasorb HP (polyquaternium 59).

The coloring agents, colorants or dyes used herein include natural foods colors and dyes suitable for food, drug and cosmetic applications. These colorants are also known as FD & C, and D&C dyes and lakes and are preferably water-soluble in nature. A full recitation of all FD&C and D&C dyes and their corresponding chemical structures may be found in the Kirk-Othmer Encyclopedia of Chemical Technology, Volume 5, pages 857-884, which text is accordingly incorporated herein by reference. These coloring agents may be incorporated in amount up to about 3%, more particularly up to about 2%, and in some cases less than about 1% by weight of the personal care compositions.

In preparing personal care composition herein, it is preferred to add suitable thickening agents wherever required to provide a desirable consistency to the appropriate formulation. Examples of useful thickening agents include carboxyvinyl polymers, carrageenan, hydroxyethyl cellulose, hydrophobically modified hydroxy-ethyl-cellulose, laponite and water soluble salts of cellulose ethers such as sodium carboxymethylcellulose and sodium carboxymethyl hydroxyethyl cellulose, copolymers of lactide and glycolide monomers, carbomers. Natural gums such as gum karaya, xanthan gum, gum arabic, Guars, HP Guars, and gum tragacanth can also be used.

The term "sequestering agent" or "chelating agent" as used herein relates to a compound which is capable of bonding or complexing a metal ion between two or more atoms of the compound, thereby neutralizing or controlling harmful effects of such metal ions. Wherein holding or bonding of a metal ion is through combination of one or more different types of bonds including coordination and/or ionic bonds. Further, the information on sequestering and chelating agents that are considered for the present application is duly disclosed in T. E. Furia, CRC Handbook of Food Additives, $2^{nd}$ Edition, pp. 271-294 (1972), and M. S. Peterson and A. M. Johnson (Eds.), Encyclopedia of Food Science, pp. 694-699 (1978) are incorporated herein by reference in its entirety.

A perfume or fragrance obtained from natural or synthetic source can be employed in the present personal care composition. The fragrance may be used along with a suitable solvent, diluents or carrier. Fragrances may be added in any conventionally known method, for example, admixing to a composition or blending with other ingredients used to form a composition, in amounts which are found to be useful to increase or impart the desired scent characteristics to the disinfectant or cleaning compositions. Fragrances for the present application can be one or more selected from the following non-limiting group of compounds such as essential oils, absolutes, resinoids, resins, concretes, hydrocarbons, alcohols, aldehydes, ketones, ethers, acids, esters, acetals, ketals, nitriles, including saturated and unsaturated compounds and aliphatic, carbocyclic and heterocyclic compounds.

Another embodiment of the present application provides a method for treating or fixing regular or damaged keratin substrate comprising contacting said keratin substrate with an effective amount of personal care composition comprising: (a) a conditioning, color protecting and/or styling terpolymer of (i) about 50 wt. % to 99 wt. % of acrylamidopropyl trimethylammonium chloride (APTAC); (ii) about 0.1 wt. % to 30 wt. % of an anionic monomer selected from the group consisting of (a) acrylic acid (AA), (b) acrylamido methylpropyl sulfonate (AMPS) or (c) sodium methyl allyl sulfonate (SMAS); and (iii) about 0.1 wt. % to 20 wt. % of methacryloylaminopropyl lauryl-dimethyl ammonium chloride (MAPLDMAC), a hydrophobically modified cationic monomer; wherein said terpolymer has a cationic degree of substitution (Cat-DS) of greater than about 0.001 units, and wherein the cationic charge density is in the range of about 1 meq/g to about 6 meq/g.

According to another embodiment of the present application, it is provided with a method for washing or caring a keratin substrate comprising applying an effective amount of composition comprising a conditioning and/or styling terpolymer of (i) about 50 wt. % to 99 wt. % of acrylamidopropyl trimethylammonium chloride (APTAC); (ii) about 0.1 wt. % to 30 wt. % of an anionic monomer selected from the group consisting of (a) acrylic acid (AA), (b) acrylamido methylpropyl sulfonate (AMPS) or (c) sodium methyl allyl sulfonate (SMAS); and (iii) about 0.1 wt. % to 20 wt. % of methacryloylaminopropyl lauryl-dimethyl ammonium chloride (MAPLDMAC), a hydrophobically modified cationic monomer; wherein said terpolymer has a cationic degree of substitution (Cat-DS) of greater than about 0.001 units, and wherein the cationic charge density is in the range of about 1meq/g to about 6 meq/g.

Still another important embodiment of the present application provides a method of protecting dyed hair color from fading or wash-out during exposure to air and/or shampooing which comprising contacting/treating said dyed hair with an effective amount of personal care composition comprising a conditioning, color protecting and/or styling terpolymer of (i) about 50 wt. % to 99 wt. % of acrylamidopropyl trimethylammonium chloride (APTAC), a cationic monomer; (ii) about 0.1 wt. % to 30 wt. % of an anionic monomer selected from the group consisting of (a) acrylic acid (AA), (b) acrylamido methylpropyl sulfonate (AMPS) or (c) sodium methyl allyl sulfonate (SMAS); and (iii) about 0.1 wt. % to 20 wt. % of methacryloylaminopropyl lauryl-dimethyl ammonium chloride (MAPLDMAC), a hydrophobically modified cationic monomer; wherein said terpolymer has a cationic degree of substitution (Cat-DS) of greater than about 0.001 units, and wherein the cationic charge density is in the range of about 1 meq/g to about 6 meq/g.

The effective amount of terpolymer or tetrapolymer required for a personal care composition to protect, treat, fix or wash a damaged keratin substrate is in the range of from about 0.01 wt. % to about 15.0 wt. %, and preferably in the range of from about 0.2 wt. % to about 5.0 wt. % of the total composition.

Further, certain aspects of the present invention are illustrated in detail by way of the following examples. The examples are given herein for illustration of the invention and are not intended to be limiting thereof.

Materials, Hair Color and Interpretation of Results:

Materials: The medium density platinum bleached hair (6" length) from International Hair Importers was procured. The hair tresses were cut to 0.5 inches in width and weight approximately 2.97 grams. Wherein, textures and tones permanent hair color (Shade 4R, Red Hot Red) was measured using HunterLab Colorimeter.

Hair Color: Ammonia-free hair color: Textures & Tones 4R Red Hot Red (P&G); Ammonia-based hair color: Igora 6.88, Igora 5.99, Redken Chromatics 5C.

Interpreting the results: Color measurements ($L^*$, $a^*$, $b^*$) were taken on each tress right after dyeing. $L^*$, $a^*$, $b^*$ values were measured on each tress after one, three, five and ten wash/treatment cycles. These values were compared to the initial $L^*$, $a^*$, $b^*$ values for the tress, and $\Delta E^*$ was calculated for each tress. Each tress served as its own control. 10 measurements were taken for each tress. $\Delta E^*$ was calculated based on the initial value of the tress. The $\Delta E^*$ reported is the average $\Delta E^*$ for 3 tresses. The smaller the $\Delta E^*$ value, the smaller the color change, and better the color protection.

$$\Delta E^* = \sqrt{\Delta L^* + \Delta a^* + \Delta b^*}$$

Where: $\Delta L^* = L^*_T - L^*_{Initial}$; $\Delta a^* = a^*_T - a^*_{Initial}$; $\Delta b^* = b^*_T - b^*_{Initial}$ $$\% \text{ Color protection} = \frac{\Delta E^*_{sample} - \Delta E^*_{control}}{\Delta E^*_{control}} \times 100$$

Platinum bleached hair was chosen as the ideal hair to test color protection, because bleached hair loses more color faster than undamaged hair. Hair that has been undergone additional chemical treatment prior to coloring is more porous and the surface is more damaged than undamaged hair or non-chemically damaged hair.

Hair tresses have been colored with Textures and Tones 4R and washed with control shampoo a total of 10 times. Below are the $\Delta E^*$ values that reflect the color change for the chemically untreated vs. bleached hair tress (Table 1). The bleached hair tress lost 62% more color after 10 washes than the undamaged hair.

TABLE 1

| No of washes | $\Delta E^*$ Values | |
|---|---|---|
| | $\Delta E^*$Brown Hair | $\Delta E^*$Bleached Hair |
| 1x wash | 0.1 | 1.72 |
| 5x wash | 1.97 | 6.14 |
| 10x wash | 5.34 | 8.68 |

It should be noted that the polymers are meant to be used in combination with other cationic ingredients. To this end, we tried the color protection performance in conditioner bases that are mimic finished formulas and tried the performance of the terpolymer in finished commercially available compositions. Such commercial compositions are typically a combination of alkyl quaternary ammonium compounds (e.g. Cetrimonium Chloride, Behentrimonium Chloride) to provide the conditioning benefit and silicones (such as dimethicone) to provide conditioning and color protection benefit. Further, it is important to assess the effect of the terpolymer in the presence of cationics and silicones, as this is a good indicator of its performance in finished products.

Example 1: Procedure for Shampoo with Conditioner Regimen Procedure

Rinse the hair for 30 seconds under running water (38 C, 4 L/min), (ii) massage with 0.5 mL shampoo into hair for 30 seconds followed by (iii) the hair was again rinsed for 30 seconds, (iv) apply 0.5 mL conditioner onto the hair and leave on for 30 seconds (v) the hair was rinsed again for 30 seconds, (vi) the hair was air dried or the hair tress was kept in 50 C oven for 2 hours to dry, and (vii) repeat the above steps (i-vi) for ten times (Table 2 and Table 3).

TABLE 2

Test shampoos and conditioners compositions used in experiments

| Ingredients | Control Shampoo Weight % | Shampoo A Weight % | Shampoo B Weight % | Shampoo C Weight % | Shampoo D Weight % |
|---|---|---|---|---|---|
| Deionized Water | 84.99 | 83.99 | 83.99 | 83.99 | 83.99 |
| Disodium EDTA | 0.10 | 0.10 | 0.10 | 0.10 | 0.10 |
| Sodium Laureth Sulfate (1M EO) | 12.00 | 12.00 | 12.00 | 12.00 | 12.00 |
| Cocamidopropyl Betaine | 2.00 | 2.00 | 2.00 | 2.00 | 2.00 |
| Optiphen MIT Ultra | 0.20 | 0.20 | 0.20 | 0.20 | 0.20 |
| Citric Acid (10% solution) | — | — | — | — | — |
| Sodium Hydroxide (10% solution) | — | — | — | — | — |
| Sodium Chloride | 0.71 | 0.71 | 0.71 | 0.71 | 0.71 |
| Polymer 129 | — | 1.00 | — | — | — |
| Polymer 142 | — | — | 1.00 | — | — |
| CS00011-168 | — | — | — | 1.00 | — |
| CS00011-171 | — | — | — | — | 1.00 |
| | pH = 5.0-6.0 | pH = 5.0-6.0 | pH = 5.0-6.0 | pH = 5.0-6.0 | pH = 5.0-6.0 |

TABLE 3

Conditioner compositions used in experiments

| Ingredients | Control Conditioner Weight % | Conditioner A Weight % | Conditioner B Weight % | Conditioner C Weight % | Conditioner D Weight % |
|---|---|---|---|---|---|
| Deionized water | 85.76 | 84.76 | 84.76 | 84.76 | 84.76 |
| Cetrimonium Chloride | 3.45 | 3.45 | 3.45 | 3.45 | 3.45 |
| Cetyl Alchol | 5.00 | 5.00 | 5.00 | 5.00 | 5.00 |

TABLE 3-continued

Conditioner compositions used in experiments

| Ingredients | Control Conditioner Weight % | Conditioner A Weight % | Conditioner B Weight % | Conditioner C Weight % | Conditioner D Weight % |
|---|---|---|---|---|---|
| Stearamidopropyl dimethylamine | 1.00 | 1.00 | 1.00 | 1.00 | 1.00 |
| Stearyl Alcohol | 2.00 | 2.00 | 2.00 | 2.00 | 2.00 |
| Lactic Acid | 0.54 | 0.54 | 0.54 | 0.54 | 0.54 |
| Dimethicone | 1.00 | 1.00 | 1.00 | 1.00 | 1.00 |
| Propylene Glycol | 0.50 | 0.50 | 0.50 | 0.50 | 0.50 |
| Optiphen | 0.75 | 0.75 | 0.75 | 0.75 | 0.75 |
| Polymer 129 | — | 1.00 | — | — | — |
| Polymer 142 | — | — | 1.00 | — | — |
| CS00011-168 | — | — | — | 1.00 | — |
| CS00011-171 | — | — | — | — | 1.00 |
|  | pH = 3.5-4.5 | pH = 3.5-4.5 | pH = 3.5-4.5 | pH = 3.5-4.5 | pH = 3.5-4.5 |

Example 2: Evaluation of Color Protection with Various Polymers

Polymers having various monomer ratios were evaluated to optimize polymer for color protection benefits, and wherein, the preferred or representative ratio of APTAC/AMPS/MAPLDMAC for the present application is from about 97.7/about 0.5/about 1.8 (Table 4).

TABLE 4

Polymer Compositions with varying monomer ratios

| Polymer # | Composition (APTAC/AMPS/MAPLDMAC) |
|---|---|
| Polymer 129 | 97.7/0.5/1.8 |
| Polymer 142 | 96.2/2/1.8 |
| Polymer 168 | 93.2/5/1.8 |
| Polymer 171 | 88.2/10/1.8 |

The hair tresses were colored with Textures & Tones 4R (Red Hot Red) hair color, air dried for 48 hours and then treated with one of the following regimen:

Control Regimen=Control Shampoo+Control Conditioner

Regimen A: Shampoo A+Conditioner A (containing Polymer 129)

Regimen B: Shampoo B+Conditioner B (containing Polymer 142)

Regimen C: Shampoo C+Conditioner C (containing Polymer 168)

Regimen D: Shampoo D+Conditioner D (containing Polymer 171)

Shampoo and conditioner regimens containing polymers have demonstrated very good protection as compared to the regimen that did not contain any polymer (Table 2). The best color protection results were achieved with regimen that contained Polymer 129. The color protection test results are provided in Table 5 and FIG. 1.

Example 3: Hydrophobicity Determination by Contact Angle Measurement

Figure 2:
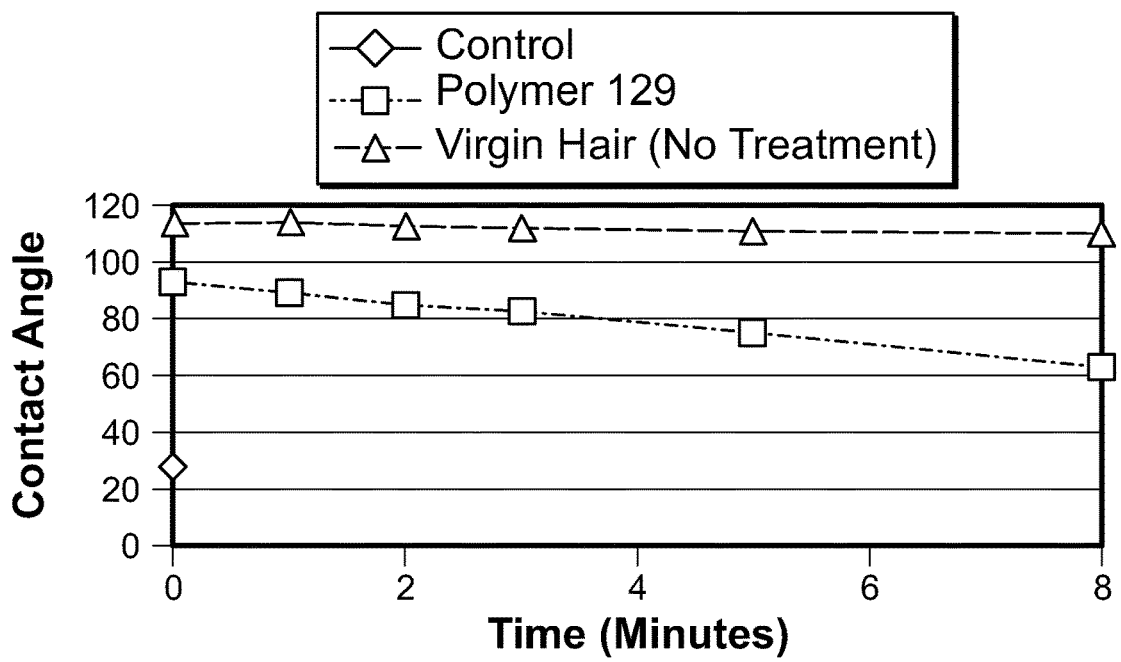
FIG. 2 is a Pseudo-static contact angle of hair after 10× washing/conditioning cycles.

Contact angle is the indication of the surface hydrophobicity of hair. The immediate and long-lasting hydrophobicity of the terpolymers were studied by measuring the contact angle. The higher the contact angle the more hydrophobic is the surface. The undamaged virgin brown hair is naturally hydrophobic, but all the chemical treatments such as bleaching reduce the hydrophobicity of the hair. Contact angle was determined for tresses that were washed and conditioned 10× with Regimen A (containing Polymer 129) and control regimen. The method is as follows: A portion of the hair tress was stretched on a specially designed plate so that the fibers were suspended together in space to form a "single" surface. The image analysis and measurements were done with Kruss drop shape analysis system DSA-10. A droplet of deionized water was delivered from a syringe onto the fiber surface. Droplet mass is ~0.004 g. Images and measurements were collected at 0 seconds and in 20 second intervals until the droplet was completely absorbed by the hair and the contact angle was 0. The regimen containing polymer significantly improved the contact angle of bleached and dyed hair after 10× treatment (Table 6). The improvement in contact angle is an indication of the improvement of the condition and hydrophobicity of hair surface. It also indicates that the polymer effectively deposits onto the hair surface and it is substantive to form a hydrophobic film on the hair surface to help prevent leaching of hair color. The hydrophobicity test results are provided in Table 6 and FIG. 2.

TABLE 5

Color Protection results with different monomer ratios

| Polymer # | Regimen A Polymer 129 | Regimen B Polymer 142 | Regimen C Polymer 168 | Regimen d Polymer 171 | Control Regimen (No polymer) |
|---|---|---|---|---|---|
| APTAC/AMPS/MAPLDMAC | 97.7/0.5/1.8 | 96.2/2/1.8 | 93.2/5/1.8 | 88.2/10/1.8 | No Polymer |
| ΔE* - 1x wash/condition | 10.17 | 9.13 | 9.35 | 9.5 | 9.17 |
| ΔE* - 5x wash/condition | 17.88 | 18.62 | 18.81 | 18.77 | 19.7 |
| ΔE* - 10x wash/condition | 20.24 | 21.12 | 20.82 | 20.79 | 23.02 |

TABLE 6

Contact angle measurements

| Time (min) | Control | Polymer 129 | Virgin hair (no treatment) |
|---|---|---|---|
| 0 | 28.1 | 93.9 | 115 |
| 1 | 0 | 90.3 | 115 |
| 2 | 0 | 85.2 | 114 |
| 3 | 0 | 83.1 | 113 |
| 5 | 0 | 75.7 | 112 |
| 8 | 0 | 63.7 | 111 |

Wherein, the contact angle measurements of bleached and dyed hair treated with control shampoo and conditioner regimen, bleached and dyed hair treated 10× with shampoo and conditioner regimen containing polymer, and virgin hair (without any treatment).

Example 4: Conditioning Evaluation—Combing Force Test

To determine the conditioning properties of the polymer—bleached hair (low density, 1" with, 10" length, purchased from International Hair Importers) was treated with shampoo and conditioner.

The combing force on wet hair was measured with an Instron combing machine. For the baseline measurements, the hair was cleaned with a 4% SLES solution, rinsed, and the combing force was measured on clean hair. The hair was then treated with either the control shampoo or a shampoo containing the polymer. After shampoo was rinsed from the hair, combing force was measured again. Conditioner was applied to hair (0.2 gm conditioner/gm hair), rinsed and combing measurements were taken. Hair was then shampooed again (with the appropriate shampoo for the regimen), and the combing force was measured again. The compositions of Table 7 and Table 8 were used for this study.

Control regimen=control shampoo+control conditioner (no polymer)

Regimen E: Shampoo E (0.2% Polymer 129)+Conditioner E (1% polymer)

Regimen F: Shampoo F (1% Polymer 129)+Conditioner E (1% polymer)

The higher the combing force, the more difficult it is to detangle and comb hair. High combing forces indicate a rough hair surface, and lack of conditioning.

TABLE 7

Shampoos used for conditioning studies

| Shampoo Ingredient | Control Shampoo Weight % | Shampoo E Polymer 129 @ 0.2% Weight % | Shampoo F Polymer 129 @ 1.0% Weight % |
|---|---|---|---|
| Deionized Water | 84.99 | 84.79 | 83.99 |
| Disodium EDTA | 0.10 | 0.10 | 0.10 |
| Sodium Laureth Sulfate (1M, 70% active) | 12.00 | 12.00 | 12.00 |
| Cocamidopropyl Betaine (30% active) | 2.00 | 2.00 | 2.00 |
| Optiphen MIT Ultra | 0.20 | 0.20 | 0.20 |
| Citric Acid (10% solution) | — | — | — |
| Sodium Hydroxide (10% solution) | — | — | — |
| Sodium Chloride | 0.71 | 0.71 | 0.71 |
| Polymer 129 | | 0.20 | 1.00 |
| | pH = 5.0-6.0 | pH = 5.0-6.0 | pH = 5.0-6.0 |

TABLE 8

Conditioners used for conditioning studies

| Ingredients | Control Conditioner Weight % | Conditioner E Polymer 129 @ 1.0% Weight % |
|---|---|---|
| Deionized water | 85.76 | 84.76 |
| Cetrimonium Chloride | 3.45 | 3.45 |
| Cetyl Alchol | 5.00 | 5.00 |
| Stearamidopropyl dimethylamine | 1.00 | 1.00 |
| Stearyl Alcohol | 2.00 | 2.00 |
| Lactic Acid | 0.54 | 0.54 |
| Dimethicone | 1.00 | 1.00 |
| Propylene Glycol | 0.50 | 0.50 |
| Optiphen | 0.75 | 0.75 |
| Polymer 129 | — | 1.00 |
| | pH = 3.5-4.5 | pH = 3.5-4.5 |

TABLE 9

Combing force data for shampoos (gf-mm)

| | Shampoo E (0.2% polymer 129) | Shampoo F (1% polymer 129) | Control (shampoo with no polymer) |
|---|---|---|---|
| Baseline (clean hair) | 70305.79 | 73945.47 | 75593.34 |
| Shampoo | 19366.06 | 8545.81 | 59835.51 |

Figure 3:
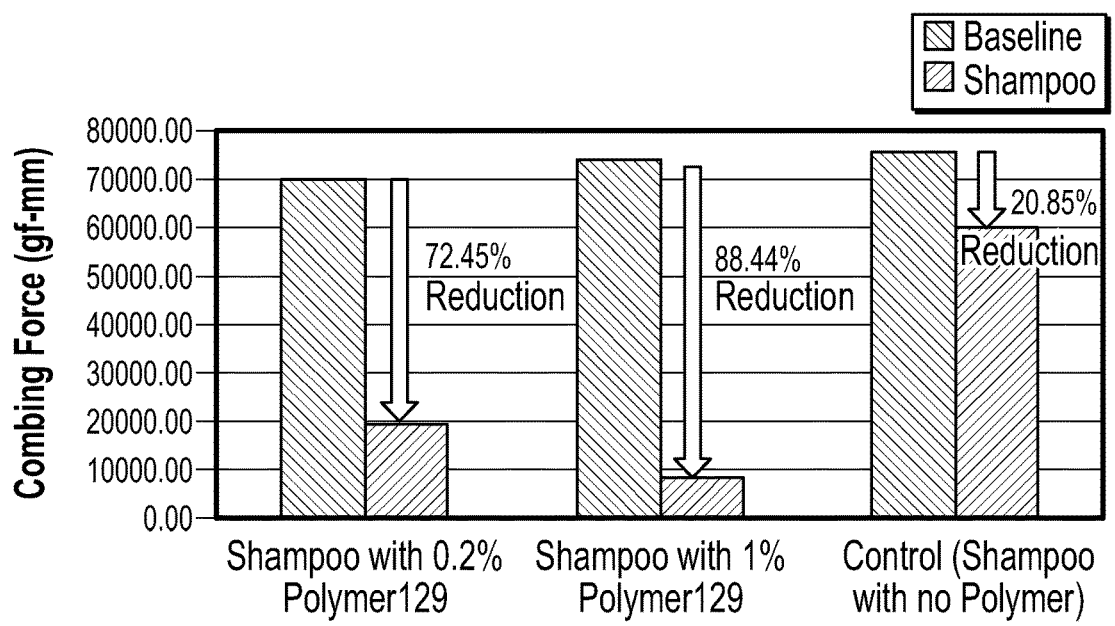
FIG. 3 is a Combing force evaluation for shampoo.
Figure 4:
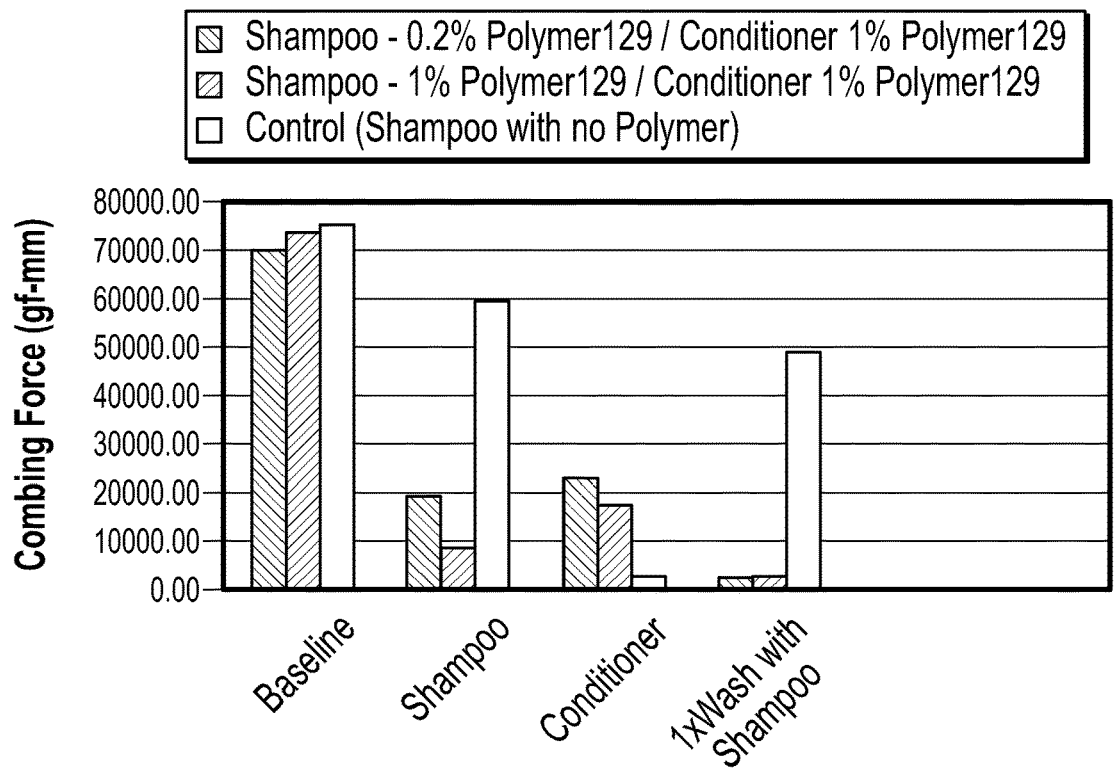
FIG. 4 is a Combing force for Polymer 129 in regimen+1× wash with shampoo

From Table 9 and Table 10 and FIG. 3-4, the addition of polymer to the shampoo caused an immediate and significant reduction in combing force, indicating very efficient conditioning of polymer.

TABLE 10

Summary of combing force data for Shampoo + Conditioner regimen

| | Regimen E (Shampoo E - 0.2% Polymer 129 Conditioner E- 1% Polymer 129) gf-mm | Regimen F (Shampoo F -1% Polymer 129 Conditioner E- 1% Polymer 129) gf-mm | Control (shampoo & conditioner without polymer) gf-mm |
|---|---|---|---|
| Baseline | 70305.79 | 73945.47 | 75593.34 |
| Shampoo | 19366.06 | 8545.81 | 59835.51 |
| Conditioner | 22905.61 | 17338.23 | 2432.09 |
| 1x wash with shampoo | 2245.27 | 2367.22 | 49145.86 |

Further, it is evident from the above results that the incorporation of polymer provides significant conditioning from both shampoo and conditioner regimens, particularly from shampoo regimen. Washing hair with the shampoo after the conditioner improves the condition of the hair. This indicates that consumers could potentially skip the conditioner at least once, and still have excellent manageability and combing of hair.

Example 5: Color Protection with Different Shades

Platinum blonde hair tresses were dyed with various shades. The tresses were then treated with Regimen A, Regimen B or Control regimen (Table 11, Table 12 and Table 13).

TABLE 11

Color Protection test with Igora 5.99

| | Igora 5.99 - Light Brown Violet (Schwarzkopf) | | | % Difference from control | |
|---|---|---|---|---|---|
| | CTR | Regimen A Polymer 129 | Regimen B Polymer 142 | Regimen A Polymer 129 | Regimen B Polymer 142 |
| ΔE*- 1x wash | 4.19 | 4.43 | 4.19 | 5.73 | 0.00 |
| ΔE*- 5x wash | 11.92 | 10.66 | 11.76 | −10.57 | −1.34 |
| ΔE*- 10x wash | 16.65 | 14.3 | 14.64 | −14.11 | −12.07 |

TABLE 12

Color Protection test with Igora 6.88

| | Igora 6.88 - Dark Blonde Red (Schwarzkopf) | | | % Difference from control | |
|---|---|---|---|---|---|
| | CTR | Regimen A Polymer 129 | Regimen BM Polymer 142 | Regimen A Polymer 129 | Regimen B Polymer 142 |
| ΔE*- 1x wash | 5.36 | 3.89 | 3.08 | −27.43 | −42.54 |
| ΔE*- 5x wash | 9.99 | 6.45 | 5.39 | −35.44 | −46.05 |
| ΔE*- 10x wash | 11.99 | 9.45 | 7.33 | −21.18 | −38.87 |

TABLE 13

Color Protection test with Redken Chromatics 5C

| | Redken Chromatics 5C - Copper (L'Oreal Group) | | | % Difference from control | |
|---|---|---|---|---|---|
| | CTR | Regimen A Polymer 129 | Regimen B Polymer 142 | Regimen A Polymer 129 | Regimen B Polymer 142 |
| ΔE*- 1x wash | 3.61 | 3.71 | 5.32 | 2.77 | 47.37 |
| ΔE*- 5x wash | 7.86 | 6.73 | 7.46 | −14.38 | −5.09 |
| ΔE*- 10x wash | 10.01 | 8.62 | 8.54 | −13.89 | −14.69 |

Example 6: Color Protection Comparison with Commercial Shampoo/Conditioner Regimens

TABLE 14

Color protection of commercial sample A

| | Commercial Sample A | | | % Difference from control | |
|---|---|---|---|---|---|
| | Shampoo + Conditioner Regimen without Polymer | Shampoo + Conditioner Regimen with Polymer 129 | Shampoo + Conditioner Regimen with Polymer 142 | Shampoo + Conditioner Regimen with Polymer 129 | Shampoo + Conditioner Regimen with Polymer 142 |
| ΔE*- 1x wash | 8.25 | 8.05 | 8.75 | −2.42 | 6.06 |
| ΔE*- 5x wash | 15.34 | 13.61 | 13.27 | −11.28 | −13.49 |
| ΔE*- 10x wash | 19.01 | 16.92 | 16.52 | −10.99 | −13.10 |

TABLE 15 color protection with commercial sample B

| | Commercial Sample B | | | % Difference from control | |
|---|---|---|---|---|---|
| | Shampoo + Conditioner Regimen without Polymer | Shampoo + Conditioner Regimen with Polymer 129 | Shampoo + Conditioner Regimen with Polymer 142 | Shampoo + Conditioner Regimen with Polymer 129 | Shampoo + Conditioner Regimen with Polymer 142 |
| ΔE*- 1x wash | 5.9 | 6.33 | 5.64 | 7.29 | −4.41 |
| ΔE*- 5x wash | 11.79 | 10.18 | 11.31 | −13.66 | −4.07 |
| ΔE*- 10x wash | 15.26 | 13.43 | 14.81 | −11.99 | −2.95 |

TABLE 16

Color protections with Commercial sample C

| | Commercial Sample C | | | % Difference from control | |
|---|---|---|---|---|---|
| | Shampoo + Conditioner Regimen without Polymer | Shampoo + Conditioner Regimen with Polymer 129 | Shampoo + Conditioner Regimen with Polymer 142 | Shampoo + Conditioner Regimen with Polymer 129 | Shampoo + Conditioner Regimen with Polymer 142 |
| ΔE*- 1x wash | 10.95 | 10.51 | 6.59 | −4.02 | −39.82 |
| ΔE*- 5x wash | 15.81 | 12.42 | 14.6 | −21.44 | −7.65 |
| ΔE*- 10x wash | 17.33 | 14.4 | 15.89 | −16.91 | −8.31 |

As seen from the results, the polymer enhanced the color protection benefit of commercial color protection shampoos and conditioner (Table 14, Table 15, and Table 16).

Example 7—Styling and Manageability in Leave-on Products

The ability of a polymer to help create and maintain the style of hair is very important.

Polymers were evaluated on 10 in long, 1 in wide hair virgin brown hair tress from International Hair Importers (IHIP). Tress were washed with a clarifying shampoo and air dried. Each tress was applied 0.5 gr of the designated 1% active polymer solution and distribute on the tress for 60 seconds. Tress were rolled onto a hair roller (2¾"×¾") to create curl. Air dry hair on rollers in 40° C. oven for 24 hours. Let tress equilibrate on rollers at room temperature for 1 hour before evaluation. Tresses were evaluated by 7 trained evaluators. Each evaluator was provided with a set of tresses, instructions on how to evaluate, scoring sheets and combs (one for each treatment). The evaluators took the hair off the rollers and hanged them for evaluation. The results were tallied and the average scores were provided.

Polymer 129 provides very good conditioning, manageability, ease of combing in leave-on treatment. It also imparts flexibility and resilience to hair as seen in the Table 17. Polymer 129 leaves a flexible film on the hair, which allows it to retain much of the stiffness and help the curl bounce back. Traditional styling polymers, are initially stiffer, but that stiffness and flexibility diminish over time.

Surprisingly, Polymer 129 provides very good static control to dry hair. One drawback of cationic polymers with high charge density is the build-up of electrostatic charge along the hair fiber. When hair is brushed or combed, especially at low humidity, the charged hair fibers repel each other, resulting in flyaway ("static"). Polymer 129, however, while having a high positive charge density, provided the best static control (less flyaway) than the other polymers evaluated.

TABLE 17

Polymer 129 Evaluation

| | Shine/Luster | Stiffness | Crunch | Stiffness X5 | Stiffness X10 | Curl Snap | Comb Drag | Residue on Comb | Residue on hair | Manageability | Static |
|---|---|---|---|---|---|---|---|---|---|---|---|
| 1% Polyquaternium-55 | 7.9 | 5.4 | 4.1 | 4.1 | 3.7 | 5.3 | 7.4 | 10.0 | 9.7 | 7.0 | 3.7 |
| 1% Polyquaternium-69 | 7.2 | 4.7 | 3.9 | 3.6 | 3.0 | 5.1 | 7.9 | 10.0 | 10 | 6.7 | 6.0 |
| 1% Acrylates Copolymer | 7.3 | 5.1 | 4.3 | 3.4 | 2.9 | 5.4 | 8.4 | 10.0 | 9.6 | 6.4 | 4.9 |
| 1% Polyquaternium-4/Hydroxypropyl Starch Copolymer | 7.6 | 5.3 | 4.0 | 3.5 | 2.9 | 5.4 | 8.3 | 10.0 | 10.0 | 5.4 | 3.7 |
| 1% Polyquaternium-11 | 7.8 | 5.9 | 4.7 | 4.2 | 3.6 | 5.4 | 7.9 | 10.0 | 9.1 | 5.9 | 4.3 |
| 1% VP/DMAPA Acrylates Copolymer | 7.7 | 6.4 | 5.0 | 4.8 | 4.0 | 5.2 | 6.7 | 9.9 | 9.4 | 6.4 | 5.9 |
| 1% Polymer 129 | 7.9 | 4.1 | 3.6 | 3.6 | 3.4 | 6.3 | 8.4 | 10.0 | 9.7 | 7.2 | 6.3 |

Example 8: Curl Holding and Defining Properties on Frizzy Hair

Polymer 129 was evaluated in a high humidity curl retention study to see the effect of polymer on curly frizzy hair. Hair was purchased from IHIP, and divided into 6" long/1" wide segments. 0.35 grams of 1% solution was applied to cleaned hair and distributed on hair for 60 seconds. Hair was rolled on ⅝" mandrel to create curl. Hair was removed from mandrel and curl was secured with a clip, then put into a 40° C. oven for 24 hours. After 24 hours, hair removed from oven. Clips were also removed, and hair was hung curl retention boards and placed in humidity chamber (80° F. and 90% relative humidity).

Curl drop was evaluated at 30 minute intervals for 4 hours.

Figure 6:
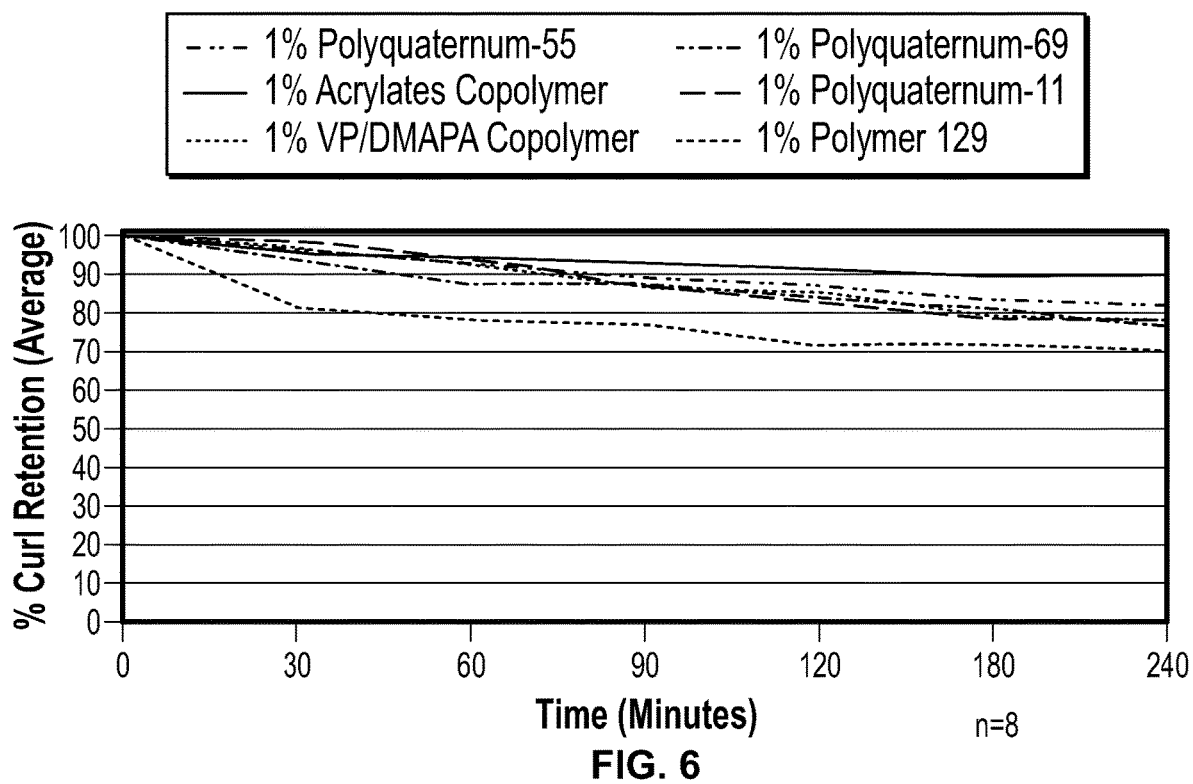
FIG. 6 is a High Humidity Curl Retention evaluation, 4-hour study (80° F., 90% RH).

All polymers showed very good curl retention at high humidity. Being a conditioning polymer, Polymer 129 imparts a soft, flexible hold to curly hair. Polymer 129 also showed very good curl definition and curl control at high humidity, comparable to traditional styling polymers (FIG. 6).

Example 9: Color Rejuvenation

A mannequin head was bleached and then colored with Textures & Tones 4R (Red hot red) hair color. The mannequin was washed and conditioned 12 times, to simulate fading. After 12 shampoo/conditioner regimen, a 1% active solution of Polymer 129 was applied to the hair. The color was evaluated with hyperspectral imaging This new technique expands on classical imaging by combining photography with spectroscopy. Where classical imaging gives a picture in which each pixel is defined by 3 values (Red, Green, Blue), hyperspectral imaging will provide a picture in which each pixel contains an entire spectrum of values for each wavelength of the integrated spectroscope. In our case, a Headwall Photonics G4-395 camera provided us with a spectrum coverage from the near UV (380 nm) until the mid-infrared (988 nm). By calibrating the camera for light source spectral intensities, we can obtain the exact spectral reflectivity spectrum of a surface, in our case, hair swatches. Lighting is placed laterally at 40 degrees from the imaging axis to avoid shine and bring out color. The absorbance spectra are shown in FIG. 5.

Each hair color (pigment) has a unique spectral absorbance signature. The higher the spectral absorbance of the red pigment, the more intense/saturated is the pigment color. Treatment with Polymer 129 increases the saturation of the red pigment, as it effectively re-saturates the red color.

Figure 7:
FIG. 7 is an Evaluation of faded hair before and after treatment with 1% Polymer 129.
Figure 8:
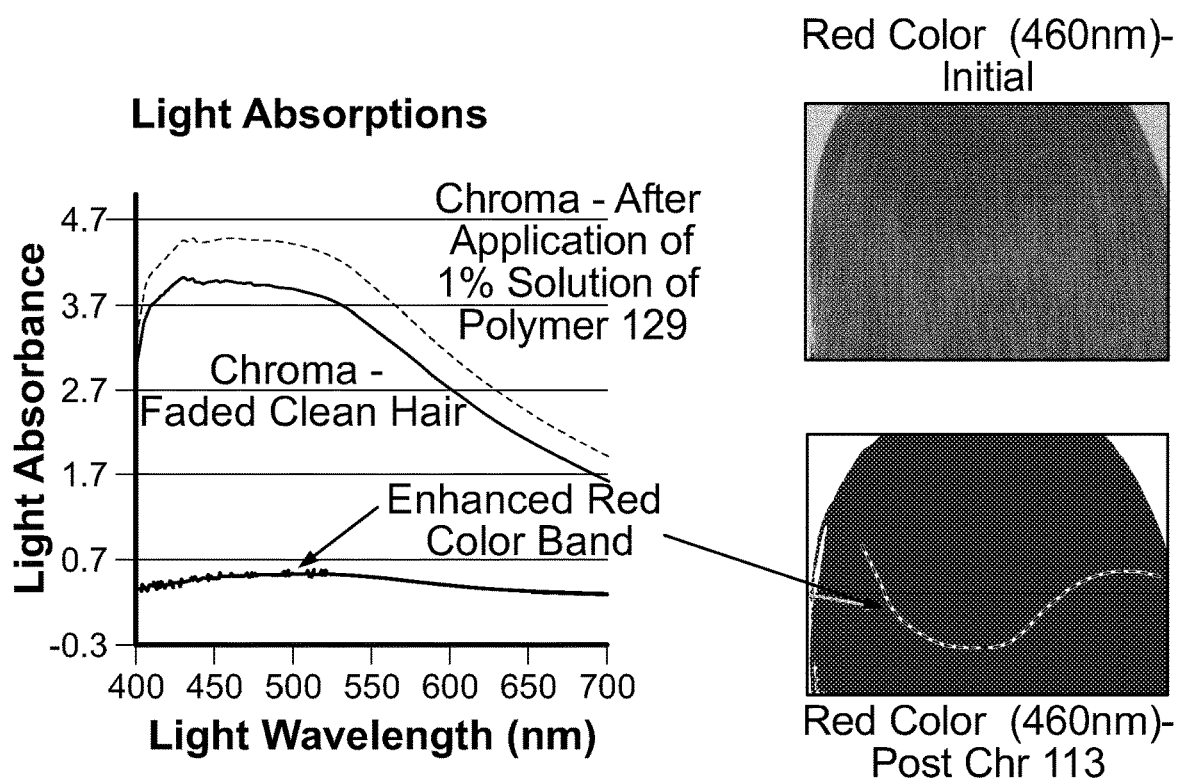
FIG. 8 is an Absorption spectra of red hair color before and after application of Polymer 129.

The blue line in FIG. 6 shows the difference between the absorption of faded hair treated with Polymer 129 and untreated hair. This line is the absorption profile of the red pigment, shows enhancement of the color pigment (FIG. 7 and FIG. 8).

Example 10: Enhancing Diameter of Hair, Volumizing Effect

The diameter of bleached hair was measured before dyeing, after dyeing, and after 1 and 5 treatments with either the control regimen of regimen F (Table 10).

The results below clearly show that the diameter of the hair treated with Regimen F has increased the diameter of the hair.

Polymer 129 forms a film on hydrophobic film on hair to help prevent water/moisture going in and of hair. Some moisture may get trapped inside the hair shaft, unable to escape due to the hydrophobic polymer film. In addition, the polymer itself also forms a uniform film on hair. Consequently, the diameter of the hair treated with Regimen F has shown an increase compared to the control regimen (Table 10).

Figure 9:
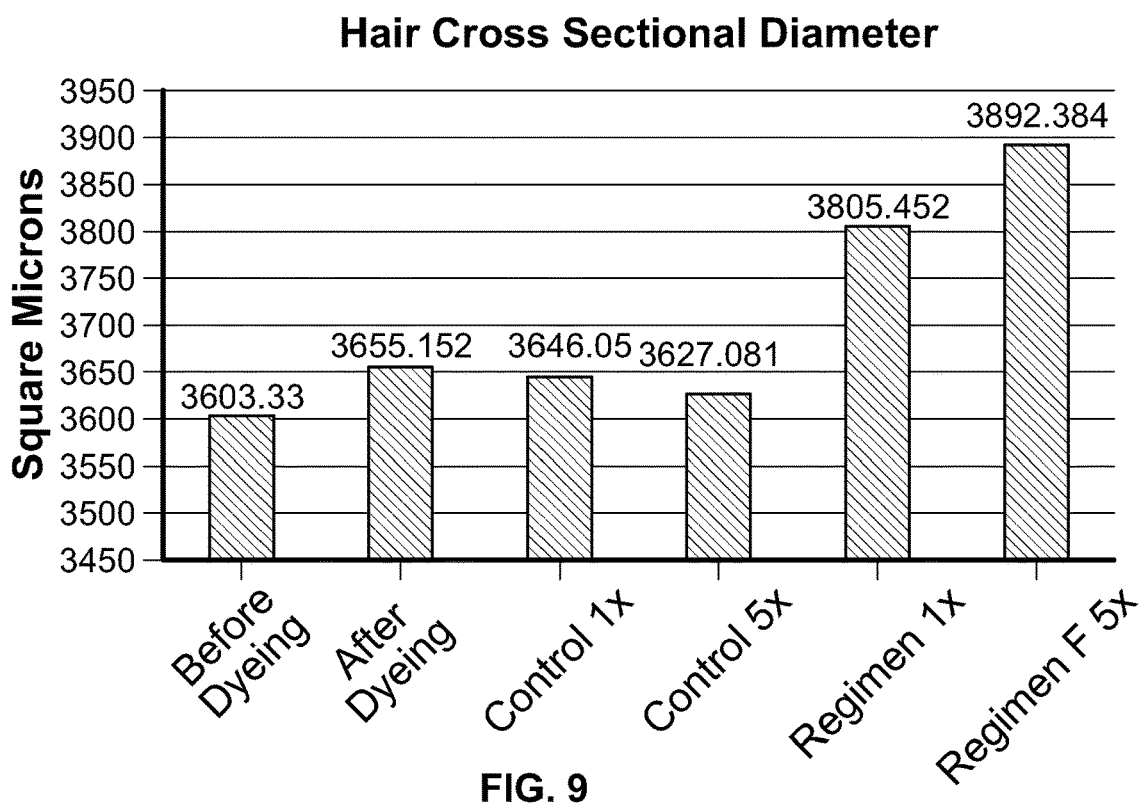
FIG. 9 is a Summary of hair cross sectional diameter measurements

There is a trend of decreasing cross section diameter for the control tress. This could be explained by further damage to the hair (eg. cuticle removal) during the washing and conditioning cycle (FIG. 9).

The increase in the diameter of the hair also resulted in a perceived volumizing effect for Regimen F.

Figure 10:
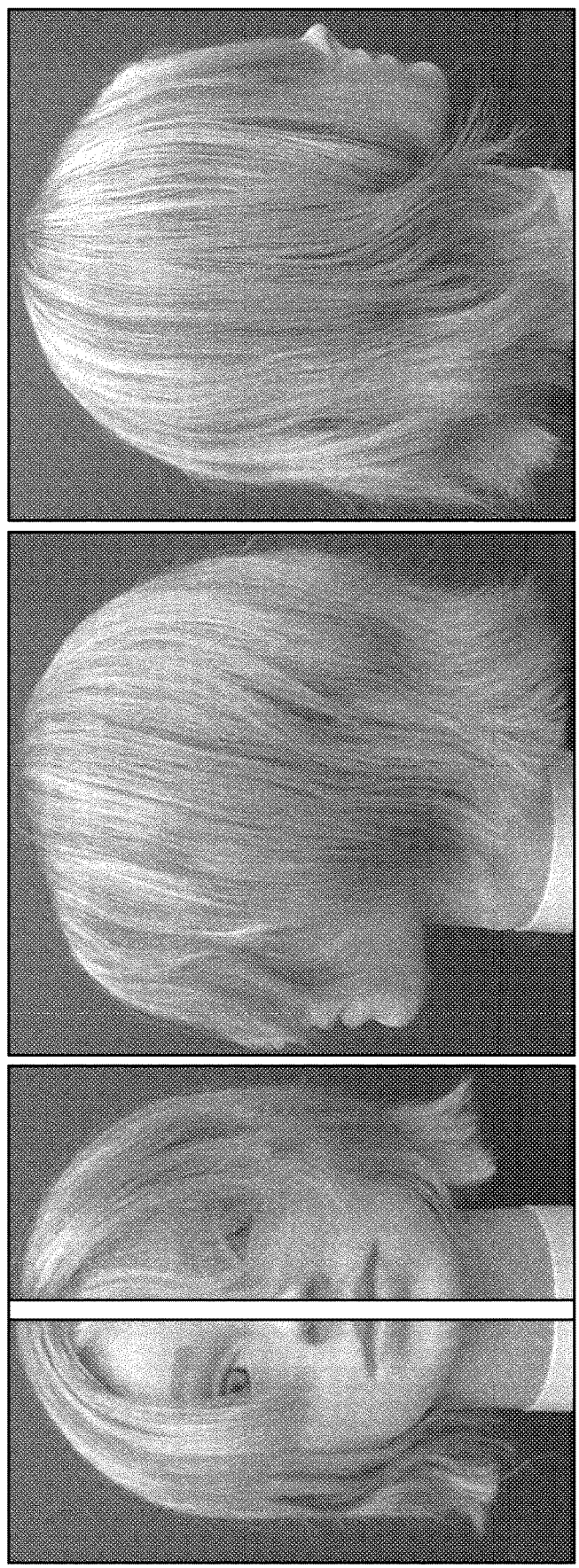
FIG. 10 is a Picture of the mannequin used for evaluation of hair volume by evaluators

During a ½ head evaluation on a mannequin, evaluators rated volume of the side treated with Regimen F higher than the side treated with the control regimen. Evaluators also perceived the side treated with Regimen F as having more hair. (FIG. 10)

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

What is claimed is:

1. A personal care conditioning, color protecting and/or styling composition for a keratin substrate comprising:
   A. at least one conditioning, color protecting and/or styling ter/tetra polymer obtained from polymerizing:
      (i) about 0.1 wt. % to 99 wt. % of acrylamidopropyl trimethylammonium chloride (APTAC), a cationic monomer;
      (ii) about 0.1 wt. % to 30 wt. % of at least one anionic monomer selected from the group consisting of (a) acrylic acid (AA), (b) acrylamido methylpropyl sulfonate (AMPS), and/or (c) sodium methyl allyl sulfonate (SMAS); and
      (iii) about 0.1 wt. % to about 20 wt. % of methacryloylaminopropyl lauryl-dimethyl ammonium chloride (MAPLDMAC), a hydrophobically modified cationic monomer;
   B. at least one cosmetically acceptable excipient; and
   C. optionally, at least one effective amount of personal care active ingredient.

2. The composition according to claim 1, wherein said keratin substrate is colored hair, uncolored hair or skin.

3. The composition according to claim 1, wherein the average molecular weight of said terpolymer is in the range of from about 100,000 to 1000,000 g/mol as determined by gel permeation chromatography.

4. The composition according to claim 1, wherein said personal care active ingredient selected from the group consisting of allantoin, tocopherol nicotinate, niacinamide, retinyl propionate, palmitoyl-gly-his-lys, phytosterol, isoflavone, dexpanthenol, panthenol, bisabolol, farnesol, phytantriol, salicylic acid, zinc/sodium pyridinethione salts, piroctone olamine, selenium disulfide, tetrahydrocurcumin, glucosamine, N-acteyl glucosamine, vitamin B3, retinoids, peptides, phytosterol, dialkanoyl hydroxyproline, hexamidine, salicylic acid, N-acyl amino acids, escolols, sunscreen actives, UV-A/UV-B protecting agent, water soluble vitamins, oil soluble vitamins, hesperedin, mustard seed extract, glycyrrhizic acid, glycyrrhetinic acid, carnosine, butylated hydroxytoluene (BHT) and butylated hydroxyanisole (BHA), ergothioneine, vanillin, vanillin derivatives, diethylhexyl syrinylidene malonate, melanostatine, sterol esters, fatty acids, poly-unsaturated fatty acids, zinc pyrithione (ZPT), anti-fungal agents, thiol compounds, N-acetyl cysteine, glutathione, thioglycolate, β-carotene, ubiquinone, amino acids, idebenone, dehydroacetic acid, Licohalcone A, creatine, creatinine, feverfew extract, yeast extract, beta glucans, alpha glucans, alone or in combination.

5. The composition according to claim 1, wherein said terpolymer (i) has a cationic degree of substitution (Cat-DS) of greater than about 0.001 units, and (ii) has a cationic charge density in the range of about 1 meq/g to about 6 meq/g.

6. The composition according to claim 1, wherein the composition is capable of fixing or treating hair conditioning/styling properties comprising detangling, wet combability, wet feel, dry combability, dry feel, sheen, static flyaway control, hydrophobicity, surface smoothening, improved deposition, no build-up, color protection, and/or curl retention.

7. The composition according to claim 1, wherein the pH of said personal care compositions is in the range of from about 3 to about 13.

8. The composition according to claim 1, wherein said cosmetically acceptable excipient is selected from the group consisting of fatty substances, gelling agents, thickeners, surfactants, moisturizers, emollients, hydrophilic or lipophilic active agents, antioxidants, sequestering agents, preserving agents, acidifying or basifying agents, fragrances, fillers, dyestuffs, emulsifying agents, solvents, UV-A or UV-B blocker/filters, plant extracts, moisturizers, proteins, peptides, neutralizing agents, solvents, silicones and/or reducing agents.

9. The composition according to claim 1 wherein said personal care composition is an appropriate product selected from the group consisting of hair-care products, shampoos, hair conditioners, leave in and rinse off conditioners, styling and treating hair compositions, hair perming products, hair relaxants, hair straightners, hair sprays and lacquers, permanent hair dyeing systems, hair styling mousses, hair gels, semi-permanent hair dyeing systems, temporary hair dyeing systems, hair bleaching systems, permanent hair wave systems, hair setting formulations, skin-care products, bath products, shower products, liquid soaps, bar soaps, fragrances and/or odoriferous ingredients consisting preparations, dentifrices, deodorizing and antiperspirant preparations, decorative preparations, light protection formulations, shaving lotions, body oils, body lotions, body gels, treatment creams, body cleaning products, skin protection ointments, shaving and aftershave preparations, skin powders, lipsticks, nail varnishes, eye shadows, mascaras, dry and moist make-up, rouge, powders, depilatory agents, sun care products, and/or compositions comprising UV blockers or UV protectors.

10. The composition according to claim 1 wherein said composition is formulated as a emulsion, a lotion, a gel, a vesicle dispersion, a paste, a cream, a solid stick, a mousse, a shampoo, and/or a spray.

11. The composition according to claim 1, wherein the effective amount of composition used in the personal care composition is in the range of from about 0.01 wt % to 10.0 wt %.

12. A conditioning, color protecting and/or styling terpolymer for a keratin substrate obtained by polymerizing:
  i. about 50 wt. % to 99 wt. % of acrylamidopropyl trimethylammonium chloride (APTAC), a cationic monomer;
  ii. about 0.1 wt. % to 30 wt. % of acrylamido methylpropyl sulfonate (AMPS), an anionic second monomer; and
  iii. about 0.1 wt. % to 20 wt. % methaacryloylaminopropyl lauryl-dimethyl ammonium chloride (MAPLDMAC), a hydrophobically modified cationic monomer;
wherein said terpolymer has a cationic degree of substitution (Cat-DS) of greater than about 0.001 units, and wherein the cationic charge density is in the range of about 1 meq/g to about 6 meq/g.

13. A conditioning, color protecting, and/or styling terpolymer for a keratin substrate comprising polymerizing:
  i. about 50 wt. % to 99 wt. % of acrylamidopropyl trimethylammonium chloride (APTAC);
  ii. about 0.1 wt. % to 30 wt. % of sodium methyl allyl sulfonate (SMAS); and
  iii. about 0.1 wt. % to 20 wt. % methacryloylaminopropyl lauryl-dimethyl ammonium chloride (MAPLDMAC), a hydrophobically modified cationic monomer;
wherein said terpolymer has a cationic degree of substitution (Cat-DS) of greater than about 0.001 units, and wherein the cationic charge density is in the range of about 1 meq/g to about 6 meq/g.

14. A conditioning, color protecting, and/or styling terpolymer for a keratin substrate comprising polymerizing:
  i. about 50 wt. % to 99 wt. % of acrylamidopropyl trimethylammonium chloride (APTAC);
  ii. about 0.1 wt. % to 30 wt. % of acrylic acid (AA); and
  iii. about 0.1 wt. % to 20 wt. % methacryloylaminopropyl lauryl-dimethyl ammonium chloride (MAPLDMAC), a hydrophobically modified cationic monomer;
wherein said terpolymer has a cationic degree of substitution (Cat-DS) of greater than about 0.001 units, and wherein the cationic charge density is in the range of about 1 meq/g to about 6 meq/g.

15. A method for treating or fixing regular or damaged keratin substrate comprising contacting said keratin substrate with an effective amount of personal care composition of claim 1 comprising:
  a conditioning, color protecting and/or styling terpolymer of
    i. about 50 wt. % to 99 wt. % of acrylamidopropyl trimethylammonium chloride (APTAC);
    ii. about 0.1 wt. % to 30 wt. % of an anionic monomer selected from the group consisting of (a) acrylic acid (AA), (b) acrylamido methylpropyl sulfonate (AMPS) or (c) sodium methyl allyl sulfonate (SMAS); and
    iii. about 0.1 wt. % to 20 wt. % of methacryloylaminopropyl lauryl-dimethyl ammonium chloride (MAPLDMAC), a hydrophobically modified cationic monomer;
wherein said terpolymer has a cationic degree of substitution (Cat-DS) of greater than about 0.001 units, and wherein the cationic charge density is in the range of about 1 meq/g to about 6 meq/g.

16. A method for washing or caring a keratin substrate comprising applying an effective amount of composition of claim 1 comprising:
  a conditioning, color protecting and/or styling terpolymer of
    i. about 50 wt. % to 99 wt. % of acrylamidopropyl trimethylammonium chloride (APTAC);
    ii. about 0.1 wt. % to 30 wt. % of an anionic monomer selected from the group consisting of (a) acrylic acid (AA), (b) acrylamido methylpropyl sulfonate (AMPS) or (c) sodium methyl allyl sulfonate (SMAS); and
   iii. about 0.1 wt. % to 20 wt. % of methacryloylaminopropyl lauryl-dimethyl ammonium chloride (MAPLDMAC), a hydrophobically modified cationic monomer;

wherein said terpolymer has a cationic degree of substitution (Cat-DS) of greater than about 0.001 units, and wherein the cationic charge density is in the range of about 1 meq/g to about 6 meq/g.

17. A process for preparing a conditioning, color protecting, and/or styling terpolymer comprising polymerizing:
   i. about 50 wt. % to 99 wt. % of acrylamidopropyl trimethylammonium chloride (APTAC), a cationic monomer;
   ii. about 0.1 wt. % to 30 wt. % of an anionic monomer selected from the group consisting of (a) acrylic acid (AA), (b) acrylamido methylpropyl sulfonate (AMPS) or (c) sodium methyl allyl sulfonate (SMAS); and
   iii. about 0.1 wt. % to 20 wt. % of a methacryloylaminopropyl lauryl-dimethyl ammonium chloride (MAPLDMAC), a hydrophobically modified cationic monomer;

wherein the prepared terpolymer has a cationic degree of substitution (Cat-DS) of greater than about 0.001 units, and wherein the cationic charge density is in the range of about 1 meq/g to about 6 meq/g.

18. The process according to claim 17, wherein the terpolymer is prepared by radical polymerization, emulsion polymerization, ionic chain polymerization, bulk polymerization, suspension polymerization or precipitation polymerization.

19. The process according to claim 17, wherein the average molecular weight of the terpolymer is in the range of from about 100,000 to 1000,000 g/mol as determined by gel permeation chromatography.

20. A method of protecting dyed hair color from fading or wash-out during exposure to air and/or shampooing which comprising contacting/treating said dyed hair with an effective amount of personal care composition of claim 1 comprising:
a conditioning, color protecting and/or styling terpolymer of
   i. about 50 wt. % to 99 wt. % of acrylamidopropyl trimethylammonium chloride (APTAC), a cationic monomer;
   ii. about 0.1 wt. % to 30 wt. % of an anionic monomer selected from the group consisting of (a) acrylic acid (AA), (b) acrylamido methylpropyl sulfonate (AMPS) or (c) sodium methyl allyl sulfonate (SMAS); and
   iii. about 0.1 wt. % to 20 wt. % of methacryloylaminopropyl lauryl-dimethyl ammonium chloride (MAPLDMAC), a hydrophobically modified cationic monomer;

wherein said terpolymer has a cationic degree of substitution (Cat-DS) of greater than about 0.001 units, and wherein the cationic charge density is in the range of about 1 meq/g to about 6 meq/g.

* * * * *